US012130216B2

(12) United States Patent
Haack et al.

(10) Patent No.: US 12,130,216 B2
(45) Date of Patent: Oct. 29, 2024

(54) SAMPLE COLLECTING DEVICE AND SAMPLE COLLECTING APPARATUS

(71) Applicant: MICRO-TECH (NANJING) CO., LTD., Jiangsu (CN)

(72) Inventors: Scott Haack, Jiangsu (CN); Jianjun Shuang, Jiangsu (CN); Zhenghua Shen, Jiangsu (CN); Weiqin Qiu, Jiangsu (CN); Jie Hu, Jiangsu (CN); Changqing Li, Jiangsu (CN); Minghao Feng, Jiangsu (CN)

(73) Assignee: MICRO-TECH (NANJING) CO., LTD., Nanjing (CN)

( * ) Notice: Subject to any disclaimer, the term of this patent is extended or adjusted under 35 U.S.C. 154(b) by 416 days.

(21) Appl. No.: 17/512,401

(22) Filed: Oct. 27, 2021

(65) Prior Publication Data

US 2022/0050032 A1 Feb. 17, 2022

Related U.S. Application Data

(63) Continuation-in-part of application No. PCT/CN2020/077318, filed on Feb. 29, 2020.

(30) Foreign Application Priority Data

Apr. 29, 2019 (CN) .......................... 201910356528.5

(51) Int. Cl.
*G01N 1/40* (2006.01)
*B01D 29/03* (2006.01)
(Continued)

(52) U.S. Cl.
CPC .......... *G01N 1/4077* (2013.01); *B01D 29/03* (2013.01); *B01D 29/96* (2013.01); *B01D 35/12* (2013.01);
(Continued)

(58) Field of Classification Search
CPC ......... G01N 1/4077; G01N 2001/4088; G01N 1/22; G01N 35/00584; G01N 33/00;
(Continued)

(56) References Cited

U.S. PATENT DOCUMENTS

| | | | | |
|---|---|---|---|---|
| 4,643,197 | A | * | 2/1987 | Greene .................... A61M 1/79 604/319 |
| 5,624,418 | A | * | 4/1997 | Shepard .................. A61M 1/79 210/85 |
| 2014/0121560 | A1 | * | 5/2014 | Parks ..................... A61B 10/02 600/562 |

FOREIGN PATENT DOCUMENTS

| | | |
|---|---|---|
| CN | 104114204 A | 10/2014 |
| CN | 106037828 A | 10/2016 |

(Continued)

OTHER PUBLICATIONS

International Search Report dated Jun. 16, 2020 in corresponding PCT application PCT/CN2020/077318.

*Primary Examiner* — Brandi N Hopkins
(74) *Attorney, Agent, or Firm* — Maier & Maier, PLLC

(57) ABSTRACT

The present application provides a sample collecting device and a sample collecting apparatus. The sample collecting device includes a housing assembly with a cavity and a filtering unit disposed in the cavity, where the housing assembly is provided with a collecting hole and a suction hole, both of which are communicated with the cavity, the suction hole is communicated with the collecting hole through the filtering unit, the housing assembly is provided with a gateway on its side wall, and at least part of the filtering unit is configured to be moved to an outside of the housing assembly through the gateway. The present application can greatly improve efficiency of sample collection and effectively save the time of medical workers.

25 Claims, 14 Drawing Sheets

(51) Int. Cl.
  *B01D 29/96*   (2006.01)
  *B01D 35/12*   (2006.01)
  *B01D 35/30*   (2006.01)

(52) U.S. Cl.
  CPC ........ *B01D 35/30* (2013.01); *B01D 2201/204* (2013.01); *G01N 2001/4088* (2013.01)

(58) Field of Classification Search
  CPC ...... G01N 35/04; G01N 35/00; G01N 1/2273; G01N 1/14; G01N 33/0009; G01N 1/2205; G01N 1/2294; B01D 29/03; B01D 29/96; B01D 35/12; B01D 35/30; B01D 2201/204; B01D 29/56; B65D 81/365
  See application file for complete search history.

(56) References Cited

FOREIGN PATENT DOCUMENTS

| | | |
|---|---|---|
| CN | 206482607 U | 9/2017 |
| CN | 107811658 A | 3/2018 |
| CN | 207707945 U | 8/2018 |
| CN | 108883212 A | 11/2018 |
| CN | 209916058 U | 4/2020 |
| WO | 2019014365 A1 | 1/2019 |

\* cited by examiner

SAMPLE COLLECTING DEVICE AND SAMPLE COLLECTING APPARATUS

CROSS-REFERENCE TO RELATED APPLICATIONS

This application is a continuation-in-part of International Application No. PCT/CN2020/077318, filed on Feb. 29, 2020, which claims the priority to the Chinese patent application No. 201910356528.5, filed on Apr. 29, 2019. Both of the aforementioned applications are hereby incorporated by reference in their entireties.

TECHNICAL FIELD

This application relates to the technical field of medical devices, specifically to a sample collecting device and a sample collecting apparatus.

BACKGROUND

Currently, a tissue sample collection and separation device has been used in clinical practice. In some cases, a tissue sample such as polyps in the patient's body needs to be collected and separated through the device for pathological analysis.

The inventor found in researches that there are at least the following shortcomings in the existing related technologies:

The sample collection process is very complicated and wastes a lot of doctor's time.

SUMMARY

The present application provides a sample collecting device and a sample collecting apparatus, which can greatly improve the efficiency of sample collection and effectively save the time of medical workers.

Embodiments of the present application can be realized as follows:

An embodiment of the present application provides a sample collecting device, which includes a cover body, a filtering structure and a bottle body in sequence, where the cover body is provided with a collecting hole, the bottle body is provided with a suction hole, and the filtering structure and the cover body are movably arranged, so that when the filtering structure is located between the cover body and the bottle body, the suction hole is communicated with the collecting hole through the filtering structure, and when the filtering structure is not completely located between the cover body and the bottle body, a sample in the filtering structure can be taken out.

Optionally, the filtering structure is rotatably connected to the cover body.

Optionally, the sample collecting device further includes a first fastener, the cover body is connected to the filtering structure through the first fastener, and the filtering structure is rotatably connected to the cover body around the axis of the first fastener.

Optionally, the cover body is provided with a first hole, the filtering structure is provided with a second hole, and the bottle body is provided with a third hole, the first fastener includes a first bolt and a first nut, the first bolt is configured to be threaded to the first nut after passing through the first hole, the second hole and the third hole.

Optionally, a plurality of filtering structures are provided, where the plurality of filtering structures are all connected through a connecting structure, and the second hole is disposed in the connecting structure.

Optionally, at least two filtering structures are provided, and the at least two filtering structures are symmetrically arranged with respective to the connecting structure. Optionally, the cover body is further provided with a fourth hole, the bottle body is further provided with a fifth hole, and the sample collecting device further includes a second fastener. The second fastener includes a second bolt and a second nut, and the second bolt is configured to be threaded to the second nut after passing through the fourth hole and the fifth hole.

Optionally, the filtering structure is slidably arranged between the cover body and the bottle body.

Optionally, an outer wall of the bottle body is connected with an enclosing member, which is configured to limit the filtering structure between the cover body and the bottle body.

Optionally, two enclosing members are provided. A first gap and a second gap are formed between the two enclosing members, and the filtering structure can be separated from the cover body through the first gap and/or the second gap.

Optionally, the enclosing member abuts against the cover body to maintain a constant spacing between the cover body and the bottle body.

Optionally, the sample collecting device further includes a third fastener, through which the cover body and the bottle body are connected.

Optionally, the cover body is provided with a seventh hole, the bottle body is provided with an eighth hole, and the third fastener includes a third bolt and a third nut, and the third bolt is configured to be connected with the third nut after passing through the seventh hole and the eighth hole.

Optionally, a sealing member is arranged on a side of the filtering structure close to the cover body, and/or a sealing member is arranged on a side of the filtering structure close to the bottle body.

Optionally, the sample collecting device further includes a light source that emits light towards the filtering structure. Optionally, the light source is connected with the bottle body.

Optionally, an outer wall of the bottle body is provided with a mounting hole, into which the light source is detachably clamped.

Optionally, the bottle body is provided with a transparent portion made of a transparent material, and the light source is connected with the transparent portion and located outside the bottle body.

Optionally, the bottle body includes a bottom wall and a first side wall, the first side wall is connected with the bottom wall, and the first side wall and the bottom wall form a suction tank with an opening on one side, the suction hole is communicated with the suction tank, and the bottom wall is the transparent portion.

Optionally, the cover body is provided with a convex lens portion made of a transparent material.

Optionally, the cover body includes a top wall and a second side wall, and the second side wall is connected with the top wall and the second side wall and the top wall form a collecting tank with an opening on one side, the collecting hole is located in the center of the top wall and communicated with the collecting tank, and the top wall is the convex lens portion.

Optionally, the filtering structure includes a filtering screen and a third side wall, the third side wall is connected with the filtering screen and the third side wall and the filtering screen form a filtering tank with an opening on one side, and the opening of the filtering tank faces towards the cover body.

Optionally, a first pipe head is arranged on a side of the cover body away from the filtering structure, the collecting hole is a pipe orifice of the first pipe head, and/or a second pipe head is arranged on a side of the bottle body away from the filtering structure, and the suction hole is a pipe orifice of the second pipe head.

Optionally, the bottle body is provided with a supporting member configured to abut against the cover body to maintain a constant spacing between the bottle body and the cover body.

An embodiment of the present application further provides a sample collecting apparatus, which includes the above sample collecting device and has all functions of the sample collecting device.

Optionally, the sample collecting apparatus further includes a collecting bottle, which includes a bottle body and a bottle lid, where the bottle body is provided with an opening adapted to the filtering structure, and the bottle lid is connected with the bottle body and configured to close the opening of the bottle body.

Specifically, in a first aspect of the present application, a sample collecting device is provided. The sample collecting device includes a housing assembly and a filtering unit, where the housing assembly has a cavity and is provided with a collecting hole and a suction hole, respectively, both the collecting hole and the suction hole are communicated with the cavity; the filtering unit is provided within the cavity; the suction hole is communicated with the collecting hole through the filtering unit; the housing assembly is provided with a gateway on its side wall; and at least part of the filtering unit is configured to be moved to the outside of the housing assembly through the gateway, so that a sample in the filtering unit can be taken out.

In a specific embodiment of the present disclosure, in a horizontal direction of the housing assembly, the filtering unit is arranged movably relative to the housing assembly.

In a specific embodiment of the present disclosure, the housing assembly includes a housing and a cover body, the cover body is arranged and covered on an open end of the housing, at least part of the filtering unit is located within the housing or the filtering unit is located between the housing and the cover body.

In a specific embodiment of the present disclosure, the collecting hole is provided on a top wall or side wall of the cover body and the suction hole is provided on a bottom wall or side wall of the housing.

In a specific embodiment of the present disclosure, the housing has the cavity, the side wall of the housing is provided with the gateway which is adapted to the filtering unit and communicated with the cavity each other, and the filtering unit is configured to be moved to the gateway relative to the housing assembly.

In a specific embodiment of the present disclosure, the filtering unit is rotatably disposed relative to the housing.

In a specific embodiment of the present disclosure, the sample collecting device includes at least two filtering units, at least one rotation assembly is provided in the housing, the rotation assembly is rotatably disposed in the cavity relative to the housing and has two oppositely arranged support portions, and the filtering unit is arranged on the support portions and detachably connected to the rotation assembly.

In a specific embodiment of the present disclosure, the rotation assembly includes a rotation member and the support portions; the support portions are provided on two opposite sides of the rotation member; the rotation member is rotatably disposed relative to the housing; the rotation member, the housing and the cover body form a suction cavity communicated with the collecting hole; the gateway is located outside the suction cavity and one of the support portions of the rotation assembly is located in the suction cavity.

In a specific embodiment of the present disclosure, the rotation member includes a rotating portion rotatably connected to the middle of the bottom wall of the housing, and is rotatable, relative to the housing, together with the rotating portion.

In a specific embodiment of the present disclosure, the rotation member has a driving portion which protrudes from the cover body, and/or a peripheral edge of the rotation member is hermetically connected with an inner side wall of the housing assembly.

In a specific embodiment of the present disclosure, a through hole is provided at bottoms of the support portions, and the suction hole is communicated with the collecting hole through the support portions and the filtering unit.

In a specific embodiment of the present disclosure, the filtering unit is slidably disposed relative to the housing.

In a specific embodiment of the present disclosure, a bearing part is provided in the housing, part of the filtering unit is supported in the cavity by the bearing part, and the filtering unit is slidably arranged relative to the gateway.

In a specific embodiment of the present disclosure, a chute adapted to the side wall of the filtering unit is provided on an inner side wall of the housing.

In a specific embodiment of the present disclosure, the height of the side wall of the filtering unit is gradually decreased in a direction toward the bearing part.

In a specific embodiment of the present disclosure, the bearing part is a step structure on the inner side wall of the housing, and the edge of the filtering unit is supported on the step structure.

In a specific embodiment of the present disclosure, the filtering unit includes a sealing end, and the filtering unit is hermetically connected with the housing at the gateway by the sealing end.

In a specific embodiment of the present disclosure, the cover body is connected to the housing and the cover body and the housing form the cavity, the gateway is formed between the housing and the cover body, and the filtering unit is located within and blocks the gateway.

In a specific embodiment of the present disclosure, a gap is provided between the cover body and the housing, and forms the gateway; and the filtering unit is disposed within the gateway and abuts against the cover body and the housing.

In a specific embodiment of the present disclosure, the filtering unit is rotatably or slidably disposed relative to the housing assembly.

In a specific embodiment of the present disclosure, the cover body is detachably connected to the housing through the first fastener, and the filtering unit is connected to the first fastener and can rotate relative to the housing assembly around the first fastener.

In a specific embodiment of the present disclosure, the sample collecting device includes at least two filtering units, which are connected to the first fastener by a connecting part, and/or, the filtering unit is symmetrically arranged with respect to the first fastener.

In a specific embodiment of the disclosure, the housing assembly further includes an enclosing member which is located between the housing and the cover body and forms the cavity along with the housing and the cover body, the enclosing member is provided with a gateway, and the filtering unit is arranged in the cavity and is slidably arranged relative to the gateway.

In a specific embodiment of the present disclosure, the filtering unit is located inside the enclosing member, the enclosing member has a first gap adapted to the filtering unit, first gap forms the gateway, and the filtering unit is configured to slide to the outside of the housing assembly through the first gap.

In a specific embodiment of the present disclosure, the enclosing member further has a second gap, which is arranged opposite to the first gap.

In a specific embodiment of the present disclosure, an opening of the second gap is smaller than that of the first gap.

In a specific embodiment of the present disclosure, the filtering unit is hermetically connected to at least one of the housing and the cover body through a sealing member.

In a second aspect of the present application, a sample collecting apparatus is provided. The sample collecting apparatus includes a collecting bottle and the sample collecting device described in any one of the above, the collecting bottle is provided with an assembly port adapted to the filtering unit of the sample collection device.

The present application provides a sample collecting device and a sample collecting apparatus. The collecting hole and the suction hole are disposed on the housing assembly, the filtering unit is disposed in the cavity of the housing assembly, and the suction hole is communicated with the collecting hole through the filtering unit. In this way, when the sample collecting device is connected to the suction device through the suction hole and enters into a patient's body, under the action of the suction device, a sample in the patient's body may be suctioned through the collecting hole onto the filtering unit, so that the sample may be separated from other impurities on the filtering unit and is intercepted by the filtering unit, thus realizing a rapid separation of the sample from the other impurities. At the same time, due to the gateway disposed on the side wall of the housing assembly, at least part of the filtering unit can be moved to the outside of the housing assembly relative to the housing assembly. In this way, only by moving the filtering unit to the outside of the housing assembly, the sample in the filtering unit can be removed quickly, which can greatly improve the collection efficiency of the sample, so as to effectively save the time of medical workers.

BRIEF DESCRIPTION OF DRAWINGS

In order to more clearly explain the technical solutions in the embodiments of the present application or the prior art, the following will briefly introduce the drawings that need to be used in the description of the embodiments or the prior art. Obviously, the drawings in the following description are some embodiments of the present application. For those skilled in the art, other drawings may be obtained according to these drawings without paying creative labor.

DESCRIPTION OF REFERENCE NUMBERS

Figure 1:
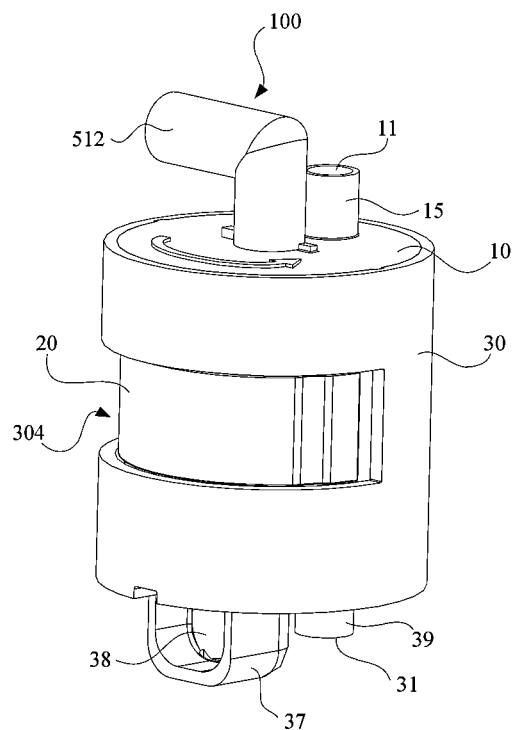
FIG. 1 is a schematic structural diagram of a sample collecting device provided in Embodiment 1 of the present application.

100—sample collecting device; 10—cover body; 11—collecting hole; 12—first hole; 13—fourth hole; 15—first pipe head; 101—top wall; 102—second side wall; 103—collecting tank;

20—filtering unit; 21—second hole; 201—filtering screen; 202—side wall; 203—filtering tank; 22—connecting part; 23—clamping part; 24—sealing end;

30—housing; 31—suction hole; 32—third hole; 33—fifth hole; 34—enclosing member; 35—first gap; 36—second gap; 37—mounting portion; 38—mounting hole; 39—second pipe head; 301—bottom wall; 302—first side wall; 303—suction tank; 304—gateway; 305—bearing part; 306—supporting member; 307—groove; 308—chute;

40—first fastener; 41—first bolt; 42—first nut; 50—rotation assembly; 51—rotation member; 511—rotating portion; 512—driving portion; 513—buckling portion; 52—support portion; 53—limit rib;
60—second fastener; 61—second bolt; 62—second nut;
70—third fastener; 71—chuck; 72—notch;
80—sealing member; 90—light source assembly; 200—collecting bottle; 210—bottle body; 220—bottle lid; 300—sample; 230—assembly port.

DESCRIPTION OF EMBODIMENTS

At present, in clinical applications, when collecting and separating polyp samples from the patient through the sample bottle, first, two ends of a sample bottle need to be communicated with an endoscopic forceps and a suction device respectively, and then under the suction effect of the suction device, a polyp tissue in the patient's body is suctioned to a filtering screen in a sample bottle through an endoscopic forceps. The polyp tissue and other impurities are separated on the filtering screen, and the polyp tissue is trapped on the filtering screen. The polyp on the filtering screen is then transferred to the collecting bottle, and sample collecting is realized in the collecting bottle for pathological analysis.

However, because the filtering screen is located in the middle of the sample bottle, it is necessary to open one end of the sample bottle prior to transferring the polyp to the collecting bottle, and then transfer the polyp tissue on the filtering screen inside the sample bottle to the collecting bottle little by little. This makes the collecting process of samples such as polyp sample in the sample bottle complicated, which causes the collection efficiency of polyp tissue to be relatively low, and wastes a lot of time for doctors.

In view of this, embodiments of the present application provide a sample collecting device and a sample collecting apparatus, where a collecting hole and a suction hole are disposed on a housing assembly, a filtering unit is disposed in the cavity of the housing assembly, and the suction hole is communicated with the collecting hole through the filtering unit. In this way, when the sample collecting device is connected to the suction device through the suction hole and enters into a patient's body, under the action of the suction device, a rapid separation of the sample and other impurities on the filtering unit can be realized. At the same time, due to a gateway disposed on a side wall of the housing assembly, at least part of the filtering unit can be moved to the outside of the housing assembly through the gateway relative to the housing assembly. In this way, compared with the existing sample bottle, the filtering unit can be moved to the outside of the housing assembly to quickly take out the sample in the filtering unit, which can greatly improve the collection efficiency of samples and effectively save the time spent by medical workers in the collection of samples such as polyp.

In order to make the purpose, technical solutions and advantages of the embodiments of the present application clearer, the technical solutions in the embodiments of the present application will be clearly and fully described in combination with the drawings in the embodiments of the present application. Obviously, the described embodiments are not all, but part of embodiments of the present application. Based on the embodiments in the present application, all other embodiments obtained by those skilled in the art without paying creative work belong to the protection scope of the present application.

Embodiment 1

Figure 2:
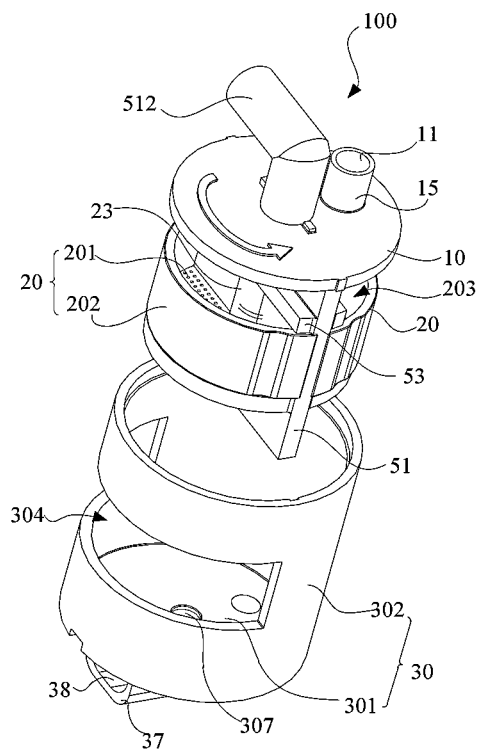
FIG. 2 is a schematic split diagram of the sample collecting device provided in Embodiment 1 of the present application from a first perspective.
Figure 3:
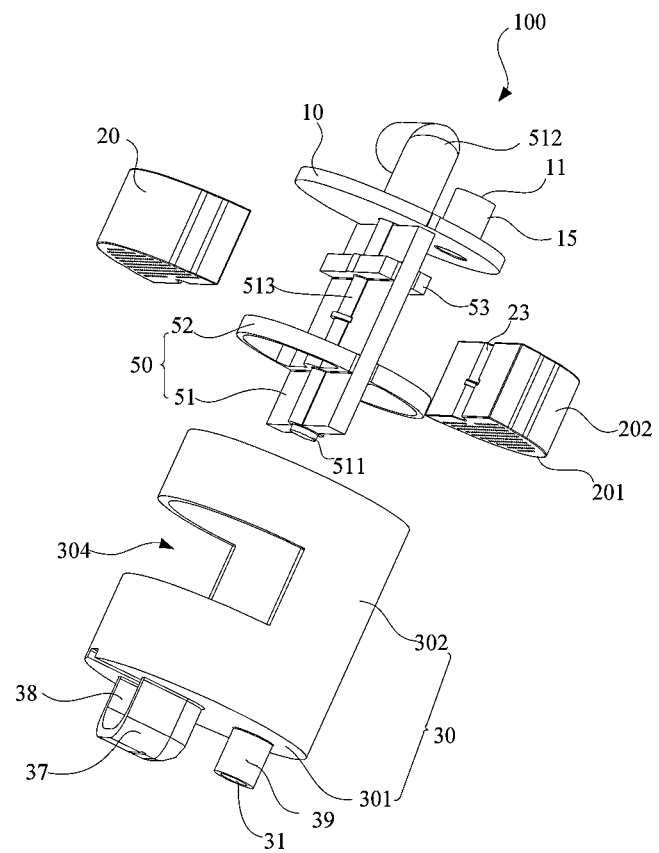
FIG. 3 is a schematic split diagram of the sample collecting device provided in Embodiment 1 of the present application from a second perspective.
Figure 4:
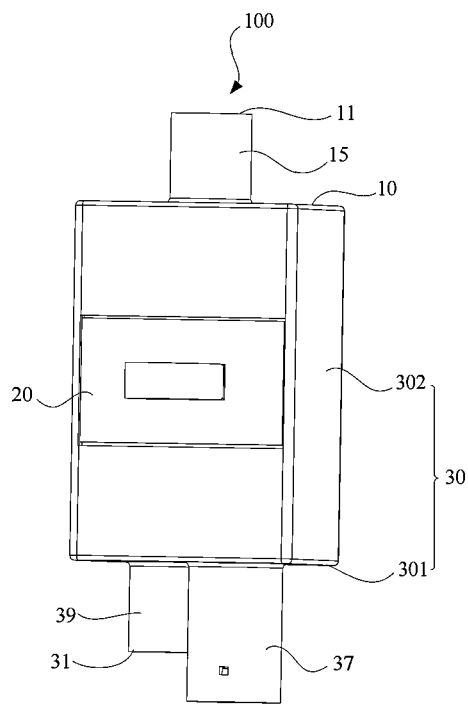
FIG. 4 is a schematic structural diagram of another sample collecting device provided in Embodiment 1 of the present application.
Figure 5:
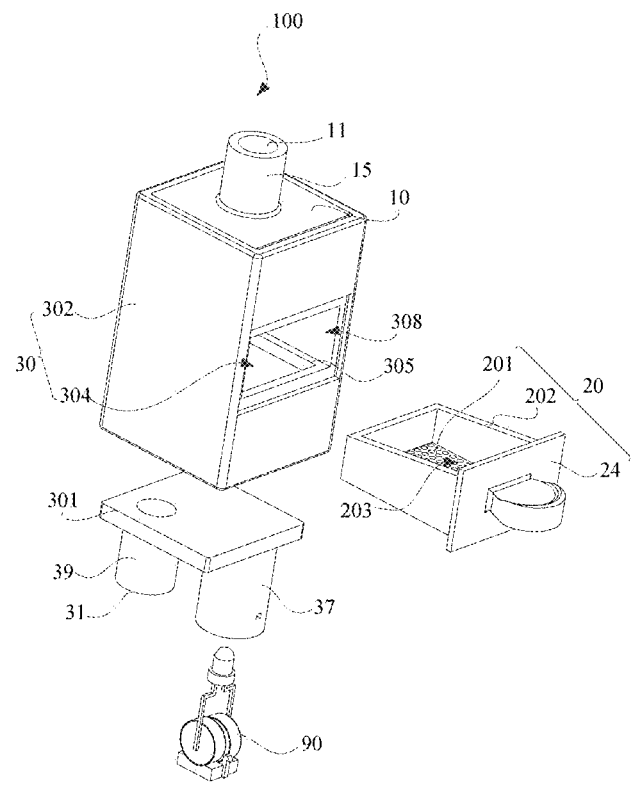
FIG. 5 is a schematic split diagram of the another sample collecting device provided in Embodiment 1 of the present application.

FIG. 1 is a schematic structural diagram of a sample collecting device provided in Embodiment 1 of the present application; FIG. 2 is a schematic split diagram of the sample collecting device provided in Embodiment 1 of the present application from a first perspective; FIG. 3 is a schematic split diagram of the sample collecting device provided in Embodiment 1 of the present application from a second perspective; FIG. 4 is a schematic structural diagram of another sample collecting device provided in Embodiment 1 of the present application; and FIG. 5 is a schematic split diagram of the another sample collecting device provided in Embodiment 1 of the present application.

Referring to FIG. 1 to FIG. 5, a sample collecting device is provided in an embodiment of the present application. As can be seen from FIGS. 1 to 5, a sample collecting device 100 includes a housing assembly and a filtering unit 20. The housing assembly has a cavity (not shown). The housing assembly is provided with a collecting hole 11 and a suction hole 31 respectively, both of which are communicated with the cavity. The filtering unit 20 is arranged in the cavity, and the suction hole 31 is communicated with the collecting hole 11 through the filtering unit 20. The side wall of the housing assembly is provided with a gateway 304, and at least part of the filtering unit 20 is configured to move to the outside of the housing assembly through the gateway 304, so that a sample in the filtering unit 20 is taken out. In this way, when the sample collecting device 100 is connected to the suction device through the suction hole 31 and enters into a patient's body, under the action of the suction device, a sample 300 in the patient's body can be suctioned onto the filtering unit 20 through the collecting hole 11, so that the sample 300 on the filtering unit 20 is separated from other impurities contained therein and the sample 300 is intercepted by the filtering unit 20, thus realizing a rapid separation of the sample 300 from other impurities contained therein, with the sample 300 being intercepted on the filtering unit 20.

At the same time, compared with existing sample collecting devices such as a sample bottle, the housing assembly of this embodiment is provided with the gateway 304 on the side wall, and the filtering unit 20 can be moved to the outside of the housing assembly through the gateway 304. Therefore, when the sample collecting device 100 of this embodiment transfers the sample 300 on the filtering unit 20, it is not necessary to open the housing assembly. Instead, the filtering unit 20 can be moved to the outside of the housing assembly through the gateway, so that the sample 300 on the filtering unit 20 can be quickly removed and transferred to a collecting bottle 200 of a sample collecting apparatus, which greatly improves the collection efficiency of the sample 300, and effectively saves the time of medical workers, such as doctors.

It should be noted that, in a normal collection and extraction process of the sample 300, the filtering unit 20 may be located in the housing assembly, so as to realize a normal collection of the sample 300, and the sample 300 is separated and intercepted by the filtering unit 20. Correspondingly, when the extraction of the sample 300 is ended and the sample 300 needs to be transferred into the collecting bottle 200 of the sample collecting apparatus, the filtering unit 20 can be moved to the outside of the housing assembly through the gateway 304. At this time, at least part of the filtering unit 20 can be located outside the housing assembly, so as to quickly take out the sample 300 on the filtering unit 20.

Generally, the sample collecting device 100 is often configured to collect and extract the sample 300 in human body, the sample 300 includes but is not limited to polyps in the human body. Exemplarily, the sample collecting device 100 is operated under an endoscope. At this time, the sample collecting device 100 is communicated with an endoscopic forceps through the collecting hole 11, and is communicated with the suction device through the suction hole 31. Under the direct view by the endoscope, the suction device is opened, and the sample 300 such as polyps in the patient's body is suctioned onto the filtering unit 20 through the endoscopic forceps channel and the collecting hole 11 under the suction action, so that the sample 300 is separated and intercepted by the filtering unit 20.

It should be noted that the collecting hole 11 may also be communicated with the endoscope forceps through other pipe, and the sample collecting device 100 is directly extended into the patient's body after being connected to the other pipe at the collecting hole 11.

Exemplarily, the suction device includes but is not limited to a vacuum generator.

Referring to FIGS. 1 to 5, the filtering unit 20 includes a filtering screen 201 and a side wall 202. The side wall 202 is connected to the filtering screen 201 and the side wall 202 and the filtering screen 201 form a filtering tank 203 having an opening on one side. The opening of the filtering tank 203 faces toward the cover body 10 or the collecting hole 11. The filtering screen 201 has a plurality of filtering holes. The sample 300 can be filtered through the filtering holes on the filtering screen 201. Under the suction action of the suction device, a fluid suctioned from the patient's body passes through the filtering unit 20, and the sample 300 is intercepted by the filtering unit 20, so that the sample 300 is retained on the filtering unit 20, and other impurities, such as substances other than the sample 300 in the fluid, are discharged from the sample collecting device 100.

As a possible embodiment, referring to FIGS. 1 to 5, the filtering unit 20 is arranged to move in a horizontal direction of the housing assembly with respect to the housing assembly. In this way, when the sample 300 in the filtering unit 20 needs to be taken out, the filtering unit 20 can be moved to the outside of the housing assembly in the horizontal direction under the action of external force, so that the sample 300 in the filtering unit 20 can be quickly removed and collected.

Alternatively, the filtering unit 20 can also be moved with respect to the housing assembly in other directions of the housing assembly, such as an inclination direction.

It should be noted that the horizontal direction is not an absolute direction, and can be understood as a direction perpendicular to a height direction of the housing assembly. Correspondingly, the inclination direction may be a direction which is inclined with respect to the height direction of the housing assembly.

In the following, by taking an example where the filtering unit 20 moves relative to the housing assembly in the horizontal direction of the housing assembly, the sample collecting device 100 of the present application is further explained.

Specifically, referring to FIGS. 1 to 5, the housing assembly includes a housing 30 (such as a bottle body) and a cover body 10 which is arranged and covered on an open end of the housing 30. At least part of the filtering unit 20 is located within the housing 30, or the filtering unit 20 is located between the housing 30 and the cover body 10. In this way, the filtering and intercepting of the sample 300 can be realized, and meanwhile the structure of the sample collecting device 100 can be made more diversified.

It should be noted that in this embodiment, the cover body 10 can also be understood as the top wall of the housing 30.

In the following embodiment, the setting pattern in which at least part of the filtering unit 20 is located within the housing 30 will be further explained.

As shown in FIGS. 1 to 5, the collecting hole 11 is provided on the cover body 10, and the suction hole 31 is provided on a bottom wall 301 or a side wall 302 of the housing 30. The housing 30 has a cavity. The side wall 302 of the housing 30 is provided with the gateway 304, which is adapted to the filtering unit 20 and communicated with the cavity. The filtering unit 20 is configured to move to the gateway 304 relative to the housing assembly. In this way, when the filtering unit 20 moves to the gateway 304, the filtering unit 20 can be moved to the outside of the housing assembly through the gateway 304, so that the sample in the filtering unit 20 can be quickly taken out of the housing assembly, which greatly improves the collection efficiency of the sample 300. Alternatively, in the embodiment of the present application, the filtering unit 20 may also be directly set in the collecting bottle 200, so as to realize the collection of the sample 300 on the filtering unit 20 in the collecting bottle 200, and there is no need to transfer the sample 300 in the filtering unit 20, and then perform collection in the collecting bottle 200, thereby greatly improving the collection efficiency of the sample 300.

It should be noted that, in order to facilitate the rapid movement of the filtering unit 20 to the outside of the housing assembly, a spacing is left between the edge of the filtering unit 20 and the gateway 304.

Referring to FIGS. 1 to 3, the filtering unit 20 is disposed rotatably relative to the housing 30. In this way, the filtering unit 20 can move to the gateway 304 by rotating.

In order to improve the extraction efficiency of the sample 300, as shown in FIGS. 2 and 3, the sample collecting device 100 may include at least two filtering units 20, and at least one rotation assembly 50 is provided in the housing 30 and rotates relative to the housing 30 in the cavity. The rotation assembly 50 has two oppositely arranged support portions 52, and the filtering unit 20 is arranged on the support portions 52 and is detachably connected to the rotation assembly 50. In this way, the filtering unit 20 can be rotated relative to the housing 30 by the rotation assembly 50, so that a filtering unit 20 bearing the sample 300 can be rotated to the gateway 304 under the drive of the rotation assembly 50 and at the same time a filtering unit 20 bearing no sample 300 can be rotated to the position opposite to the collecting hole 11 inside the housing 30 to participate in the extraction of the sample 300, thus improving the extraction efficiency of the sample 300.

It should be noted that, when there are at least two filtering units 20 in the sample collecting device 100, one filtering unit 20 participates in the extraction of the sample 300 and the remaining filtering units 20 can be used as spare filtering units.

Specifically, when there are multiple (for example, two) rotation assemblies 50 in the housing 30, two rotation assemblies 50 may cross each other and be coaxially arranged, so that the rotation assemblies 50 can rotate around the same axis. At this time, there may be multiple support portions 52, such as four or six, etc. Multiple support portions 52 may be uniformly distributed in the housing assembly.

Further, referring to FIGS. 2 and 3, the rotation assembly 50 includes a rotation member 51 and support portions 52. The support portions 52 are provided on opposite sides of the rotation member 51. The rotation member 51 is disposed rotatably relative to the housing 30. A suction cavity communicated with the collecting hole 11 is formed by the rotation member 51, the housing 30 and the cover body 10. The gateway 304 is located outside the suction cavity, and one support portion 52 of the rotation assembly 50 is located in the suction cavity. In this way, the filtering unit 20 bearing the sample 300 can be rotated to the gateway 304 through the rotation member 51, and meanwhile one spare filtering unit 20 can be rotated into the suction cavity of the housing assembly to participate in the next extraction of the sample 300.

It should be noted that, the suction cavity may be understood as a part of the above cavity. The filtering unit 20 can be rotated into the suction cavity under the drive of the rotation assembly 50 to participate in the extraction of the sample 300. As shown in FIG. 3, the rotation member 51 includes a rotating portion 511 rotatably connected to the middle of the bottom wall 301 of the housing 30, and the rotation member 51 is arranged to rotate around the rotating portion 511 relative to the housing 30. In this way, the rotation member 51 can rotate in the housing 30 around the rotating portion 511, so that the filtering unit 20 bearing the sample 300 rotates to the gateway 304 and at the same time a spare filtering unit 20 may be rotated into the suction cavity of the housing assembly.

Specifically, as shown in FIG. 2, the center of the bottom wall 301 of the housing 30 is further provided with a groove 307 adapted to the rotating portion 511. The rotating portion 511 can be embedded in the groove 307, so that the rotating portion 511 and the rotation member 51 can be assembled and positioned by the groove 307, and thereby the rotation member 51 can rotate in the housing 30 around the rotating portion 511.

In order to ensure a certain degree of air tightness in the suction cavity, the peripheral edge of the rotation member 51 is hermetically connected with the inner side wall of the housing assembly, so as to meet a certain degree of air tightness in the suction cavity. It should be noted, that the hermetical connection in this embodiment is not absolutely sealed, as long as the sample 300 can be suctioned to the filtering unit 20 in the suction cavity and the sample 300 can be separated from other impurities in the filtering unit 20.

Exemplarily, the rotation member 51 may be hermetically connected with the inner side wall of the housing assembly through a seal strip or a seal ring.

In order to facilitate the rotation of the rotation member 51, as shown in FIGS. 1 to 3, the rotation member 51 has a driving portion 512, which extends out of the cover body 10.

Exemplarily, the driving portion 512 may include but is not limited to a driving handle.

In order to facilitate the communication between the suction hole 31 and the collecting hole 11, as shown in FIG. 3, a through hole is provided at bottoms of the support portions 52, and the suction hole 31 is communicated with the collecting hole 11 through the support portions 52 and the filtering unit 20. In this way, when the filtering unit 20 is supported in the suction cavity through the support portions 52, the suction hole 31 can be communicated with the collecting hole 11 through the support portions 52 and the filtering unit 20, so as to realize the extraction of the sample 300 under the action of the suction device.

Exemplarily, the support portions 52 include but are not limited to a support ring.

As a possible embodiment, as shown in FIG. 3, a buckling portion 513 is provided on the rotation member 51, and a clamping part 23 is provided on a side of the filtering unit 20 facing the rotation member 51. When the filtering unit 20 is provided on the support portions 52, the filtering unit 20 is clamped with the buckling portion 513 through the clamping part 23, so that the filtering unit 20 is fixed relative to the rotation member 51, thereby preventing the filtering unit 20 from moving relative to the rotation assembly 50 during rotation process, and meanwhile facilitating the filtering unit 20 to be taken out from the gateway 304.

In order to prevent the filtering unit 20 from moving in a vertical direction, the rotation member 51 is further provided with a limit rib 53 located above the support portions 52. The filtering unit 20 is fixed between the limit rib 53 and the support portions 52, so that the filtering unit 20 can be limited in the vertical direction by the limit rib 53 and the support portions 52.

Exemplarily, as shown in FIGS. 2 and 3, the rotation member 51 may be a rotation plate, the peripheral edge of which is hermetically connected to the inner side wall of the housing assembly. The buckling portion 513 is a protrusion structure on one side of the rotation member 51 facing the filtering unit 20, and the clamping portion 23 is a groove adapted to the buckling portion 513.

Further, the sample collecting device 100 further includes a light source assembly 90, which is configured to emit light toward the filtering unit 20. The light source assembly 90 is provided so that a medical worker can clearly observe the sample 300 even in a dark room.

Exemplarily, the light source component 90 may be an LED lamp, which has such as its own battery and switch. The light source assembly 90 may be located in the cover body 10 or the housing 30.

As a possible embodiment, the light source assembly 90 is located outside the cavity and connected to the housing assembly; and the housing assembly has a light-transmitting part which is arranged opposite to the light source assembly 90. In this way, through setting the light-transmitting part, even if the light source assembly 90 is located outside the housing assembly, light can still be directed toward the sample 300, which is convenient for observation of medical workers.

Specifically, the light source assembly 90 can be detachably connected to the first side wall 302 or the bottom wall 301 of the housing assembly. As shown in FIGS. 1 to 5, when the light source assembly 90 is connected to the bottom wall 301 of the housing assembly, the bottom wall 301 of the housing assembly is further provided with a mounting portion 37, and the light source assembly 90 is installed in a mounting hole 38 of the mounting portion 37 and detachably connected to the bottom wall 301 of the housing assembly.

Alternatively, the light source assembly 90 may also be fixedly connected to the housing assembly by bonding or other way.

Where, the light-transmitting part may be made of a light-transmitting material. Exemplarily, the light-transmitting material includes, but is not limited to, a transparent plastic.

As shown in FIGS. 1 to 5, the housing 30 includes a bottom wall 301 and a first side wall 302. The first side wall 302 is connected to the bottom wall 301, and the first side wall 302 and the bottom wall 301 form a suction tank 303 having an opening on one side. The suction hole 31 is communicated with the suction tank 303, and the bottom wall 301 may be the above light-transmitting part.

As another possible embodiment, the light source assembly 90 may also be located inside the housing assembly. Exemplarily, the light source component 90 may be located in the housing 30 or the cover body 10. In this embodiment, the location of the light source assembly 90 is not further limited.

As shown in FIGS. 1 to 5, a first pipe head 15 is provided on a side of the cover body 10 away from the filtering unit 20, and the collecting hole 11 is a pipe orifice of the first pipe head 15. A second pipe head 39 is provided on a side of the housing 30 away from the filtering unit 20, and the suction hole 31 is a pipe orifice of the second pipe head 39. In this way, by setting the first pipe head 15 and the second pipe head 39, it is convenient for the sample collecting device 100 to be connected with other devices.

The cover body 10 may be detachably connected with the housing 30 to realize the assembling of the sample collecting device 100.

On the basis of the foregoing, another sample collection device is provided in this embodiment, and the difference from the above sample collecting device 100 is that, as shown in FIG. 4 and FIG. 5, the filtering unit 20 is slidably arranged relative to the housing 30. In this way, the filtering unit 20 can be moved to the outside of the housing assembly in a sliding manner, so that the filtering unit 20 can be directly set in the collecting bottle 200 so as to realize in the collecting bottle 200 the collection of the sample 300 on the filtering unit 20, without need to transfer the sample 300 in the filtering unit 20 prior to collecting into the collecting bottle 200, which greatly improves the collection efficiency of the sample 300.

Further, as shown in FIG. 5, a bearing part 305 is provided in the housing 30, part of the filtering unit 20 is supported in the cavity via the bearing part 305, and the filtering unit 20 is slidably arranged relative to the gateway 304. In this way, the filtering unit 20 can slide to the gateway 304 so as to move the filtering unit 20 from the gateway 304 to the outside of the housing assembly, and meanwhile make the movement of the filtering unit 20 relative to the housing 30 more convenient.

Exemplarily, the bearing part 305 may be a step structure on the inner side wall of the housing 30, and the edge of the filtering unit 20 is supported on the step structure. In this way, when the filtering unit 20 is fixed by the step structure, the collecting hole 11 and the suction hole 31 can be communicated.

Further, as shown in FIG. 5, a chute 308 adapted to the side wall 202 of the filtering unit 20 is provided on the inner side wall of the housing 30. In this way, the filtering unit 20 can realize sliding relative to the housing 30 in the chute 308, and at the same time, the chute 308 can guide a sliding direction of the filtering unit 20.

In order to ensure the airtightness of the sample collecting device 100, as shown in FIG. 5, the height of the side wall 202 of the filtering unit 20 is gradually reduced in a direction toward the bearing part 305. Correspondingly, the groove width of the chute 308 is gradually reduced in a direction in which the filtering unit 20 moves toward the housing 30.

In this way, it is beneficial to achieve a sealed connection between the filtering unit 20 and the housing assembly, and thereby the sample 300 can enter into the sample collecting device 100 under the action of the suction device.

Further, the filtering unit 20 includes a sealing end 24, by which the filtering unit 20 is hermetically connected to the housing 30 at the gateway 304. In this way, the gateway 304 can be sealed by the sealing end 24, so as to realize a sealing connection between the filtering unit 20 and the housing assembly.

Exemplarily, the sealing end 24 may be hermetically connected to the housing 30 at the gateway 304 via a sealing strip or a sealing ring.

It should be noted that, such sample collecting device 100 can be made of transparent material such as transparent plastic, semi-transparent material such as polyethylene material, or soft material with certain hardness and not easily to be deformed, such as silicone material. In this embodiment, the material of the sample collecting device 100 is not further limited.

In the embodiment of the present application, at least part of the filtering unit can be moved to the outside of the housing assembly relative to the housing assembly, which can simplify the sample collection process and facilitate the rapid transfer of samples on the filtering unit to the collecting bottle of the sample collecting apparatus, improve the efficiency of sample collection, and effectively save the time spent by medical workers in the collection of samples such as polyps. The sample collection device provided in this embodiment also has the functions of amplification and illumination, so that the doctor can clearly observe the sample on the filtering unit, even a small polyp tissue.

Embodiment 2

FIG. 6 to FIG. 16 are schematic structural diagrams of various sample collecting devices provided in the Embodiment 2 from different perspectives.

On the basis of Embodiment 1 above, a sample collecting device is provided in this embodiment. As shown in FIG. 6 to FIG. 16, the difference of the sample collecting device 100 in this embodiment from the device 100 in Embodiment 1 is that a cover body 10 is connected to a housing 30 (such as bottle body) and the cover body 10 and the housing 30 form a cavity; a gateway 304 is formed between the housing 30 and the cover body 10; and a filtering unit 20 is located in the gateway 304 and blocks the gateway 304. In this way, it can be ensured that the filtering unit 20 can be moved to the outside of the housing assembly through the gateway 304, and meanwhile the gateway 304 can be blocked by the filtering unit 20, so that the filtering unit 20 and the housing assembly can be hermetically connected to meet the air tightness requirements of the sample collecting device.

As shown in FIG. 6 to FIG. 16, there is a gap between the cover body 10 and the housing 30, and the gap form the gateway. The filtering unit 20 is provided in the gateway 304 and abuts against the cover body 10 and the housing 30. In this way, it is helpful to achieve a sealed connection between the filtering unit 20 and the housing assembly, and meantime, the filtering unit 20 can be disposed between the cover body 10 and the housing 30, so that the sample collecting device 100 has a more diversified structure.

Specifically, the filtering unit 20 is rotatably or slidably arranged relative to the housing assembly. In this way, it is possible to make the structure of the sample collecting device 100 more diversified while the sample 300 is extracted.

As a possible embodiment, referring to FIGS. 6 to 10, the cover body 10 is detachably connected to the housing 30 through a first fastener 40. The filtering unit 20 is connected to the first fastener 40 and can rotate around the first fastener 40 relative to the housing assembly. In this way, the filtering unit 20 can be rotatably connected to the housing 30 or cover body 10, so that the filtering unit 20 can be rotated to the outside of the housing assembly. By using tweezers or other tool, outside the housing assembly, a sample 300 on the filtering unit 20 is transferred to a collecting bottle 200, and meanwhile, the sample 300 on the filtering unit 20 can be quickly removed without need to open the housing assembly. At the same time, in the normal process of taking out the sample 300, the filtering unit 20 is always connected with the housing assembly, and the entire operation process of taking out the sample 300 is convenient. Since the cover body 10 is detachably connected to the housing 30 through the first fastener 40 and the filtering unit 20 is connected to the first fastener 40, it is convenient to disassemble and position the sample collecting device 100.

It should be understood that, both the cover body 10 and the filtering unit 20 can be installed and disassembled through the first fastener 40. At the same time, the first fastener 40 may also be regarded as a rotation shaft of the filtering unit 20, and thus the overall structure of the sample collecting device 100 is relatively compact.

Figure 9:
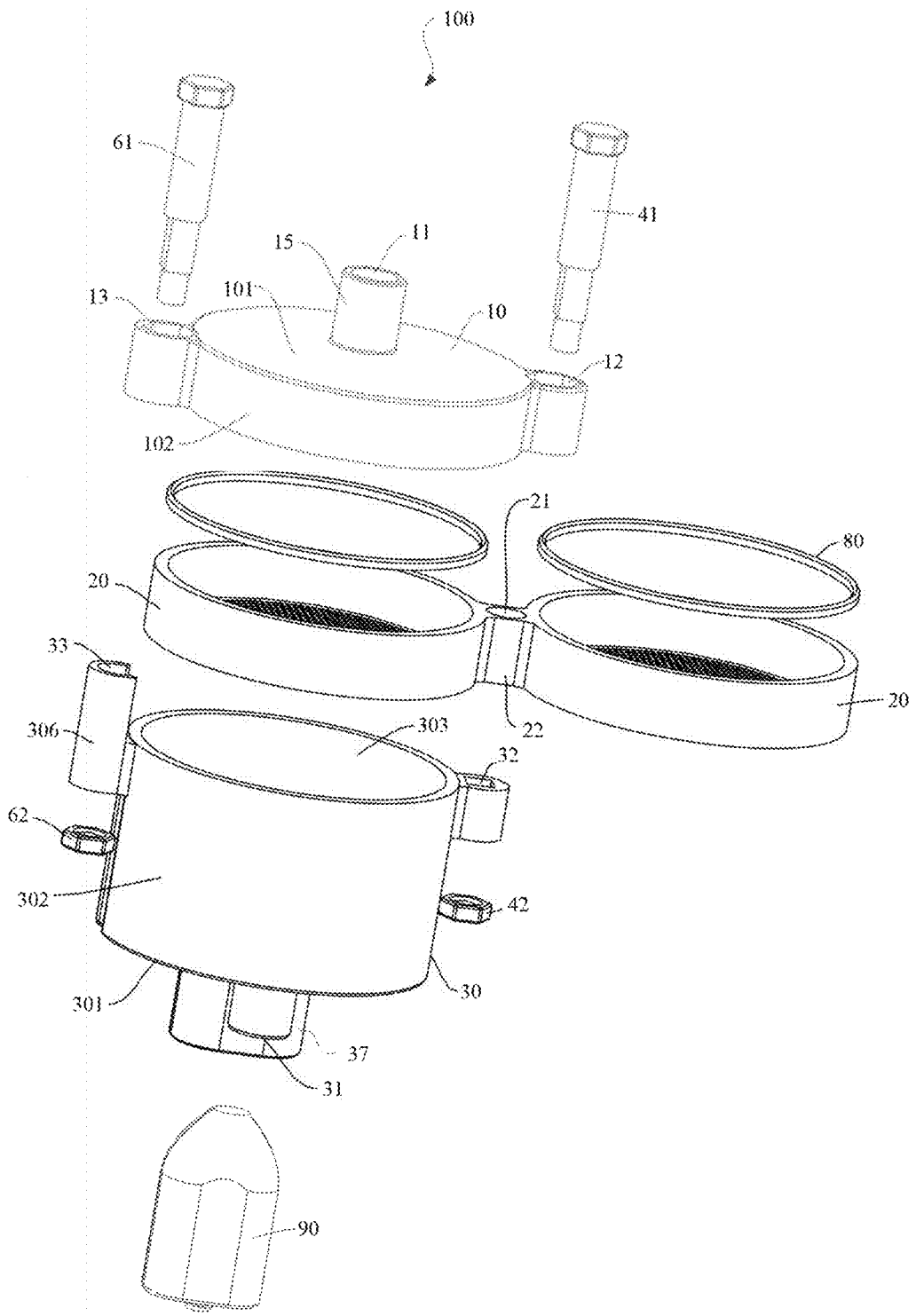
FIG. 9 is a schematic structural diagram of the sample collecting device provided in Embodiment 2 of the present application from a fourth perspective.
Figure 10:
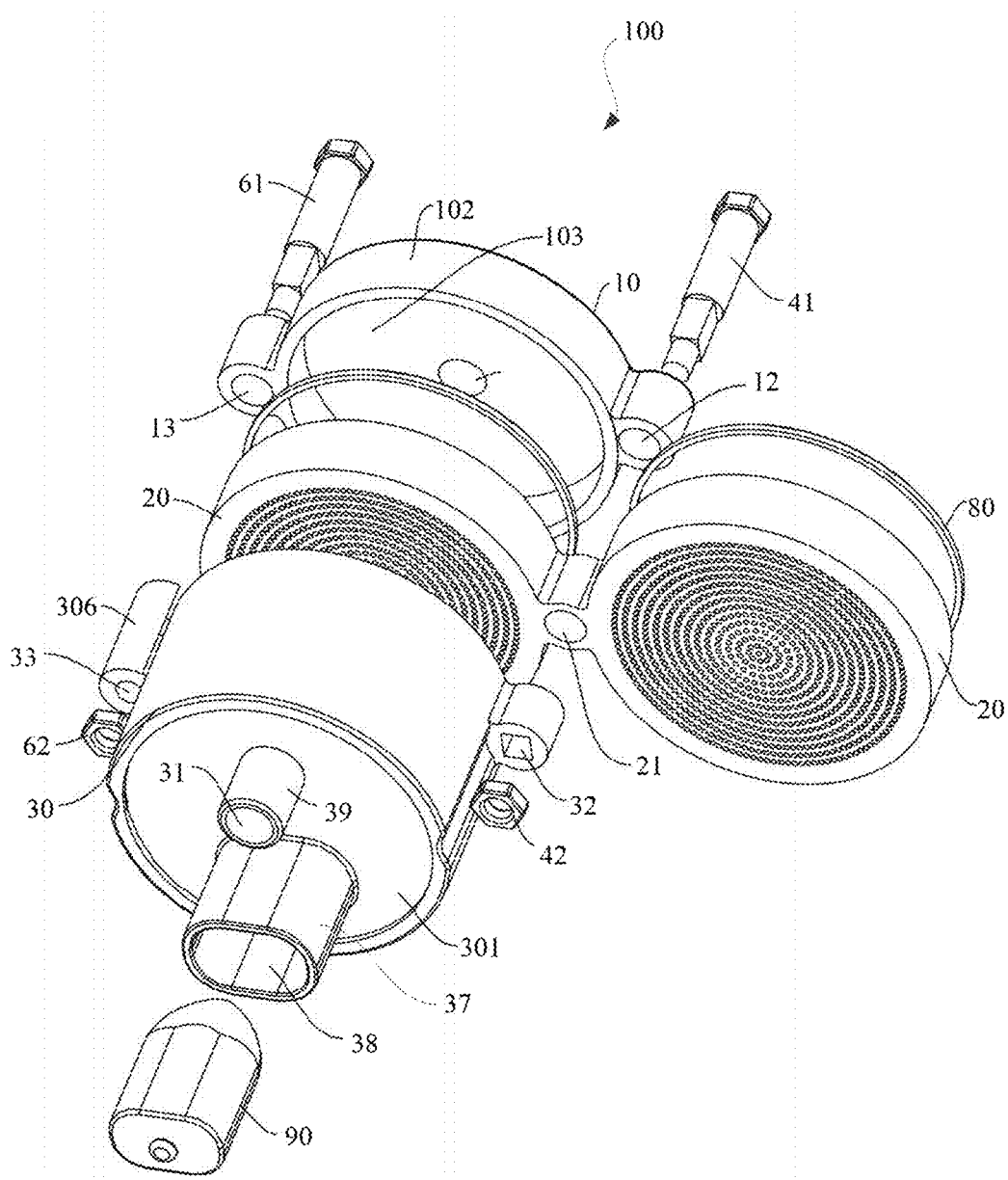
FIG. 10 is a schematic structural diagram of the sample collecting device provided in Embodiment 2 of the present application from a fifth perspective.
Figure 11:
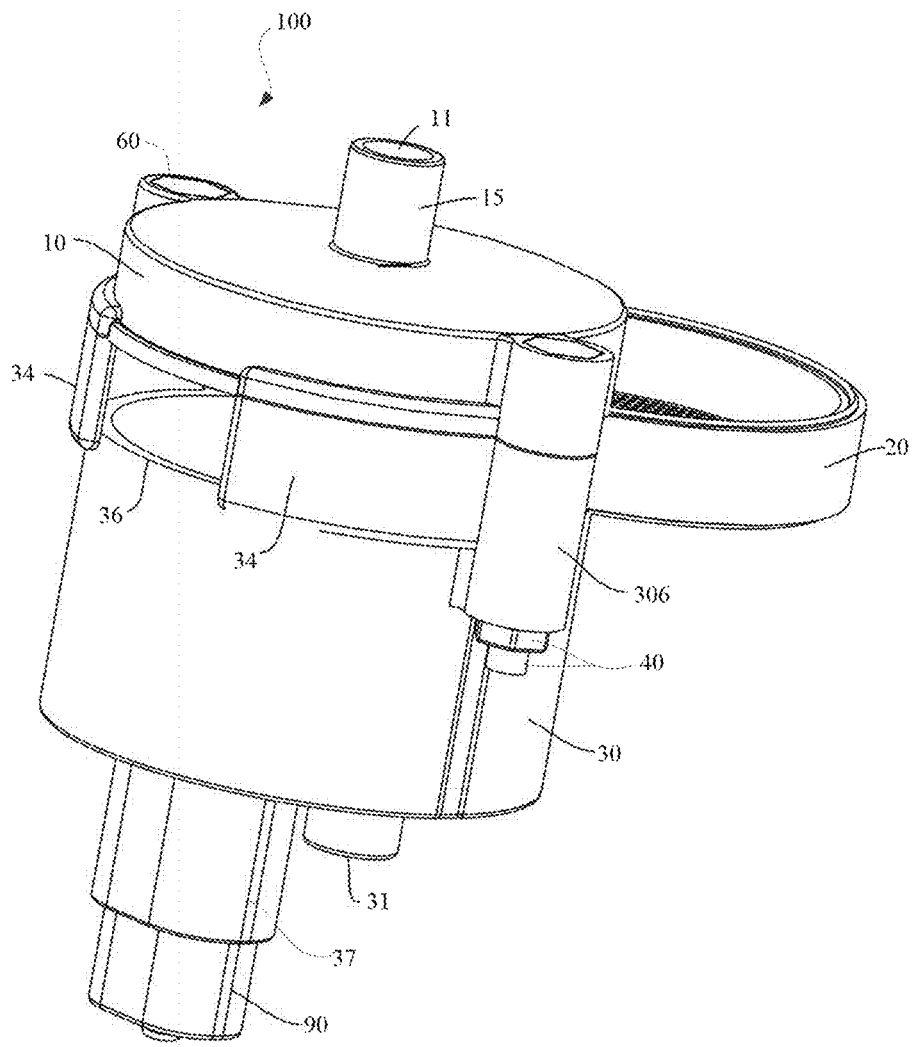
FIG. 11 is a schematic structural diagram of another sample collecting device provided in Embodiment 2 of the present application from a first perspective.
Figure 12:
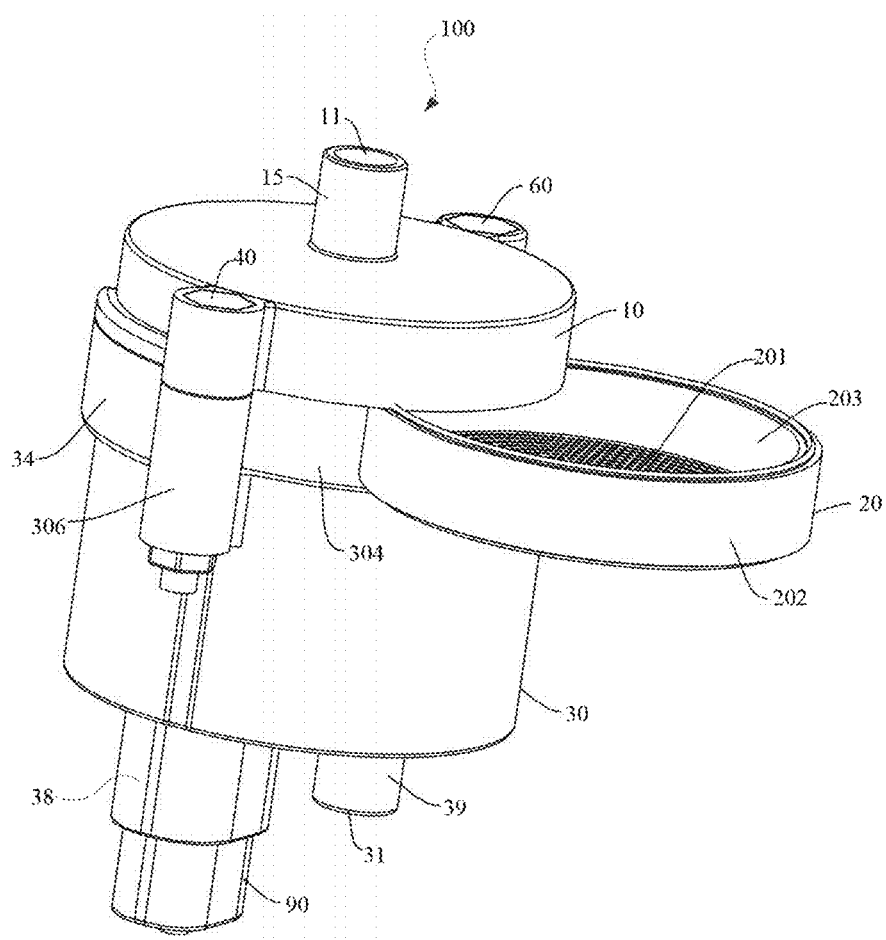
FIG. 12 is a schematic structural diagram of the another sample collecting device provided in Embodiment 2 of the present application from a second perspective.
Figure 13:
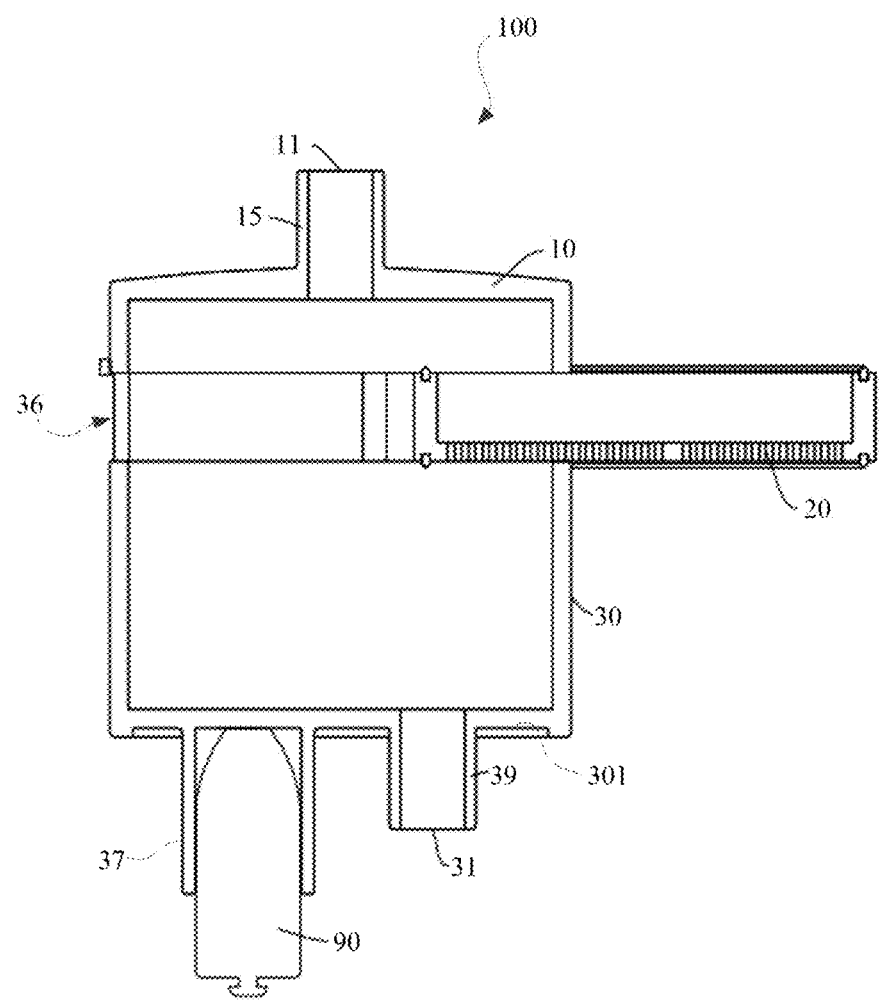
FIG. 13 is a schematic structural diagram of the another sample collecting device provided in Embodiment 2 of the present application from a third perspective.
Figure 14:
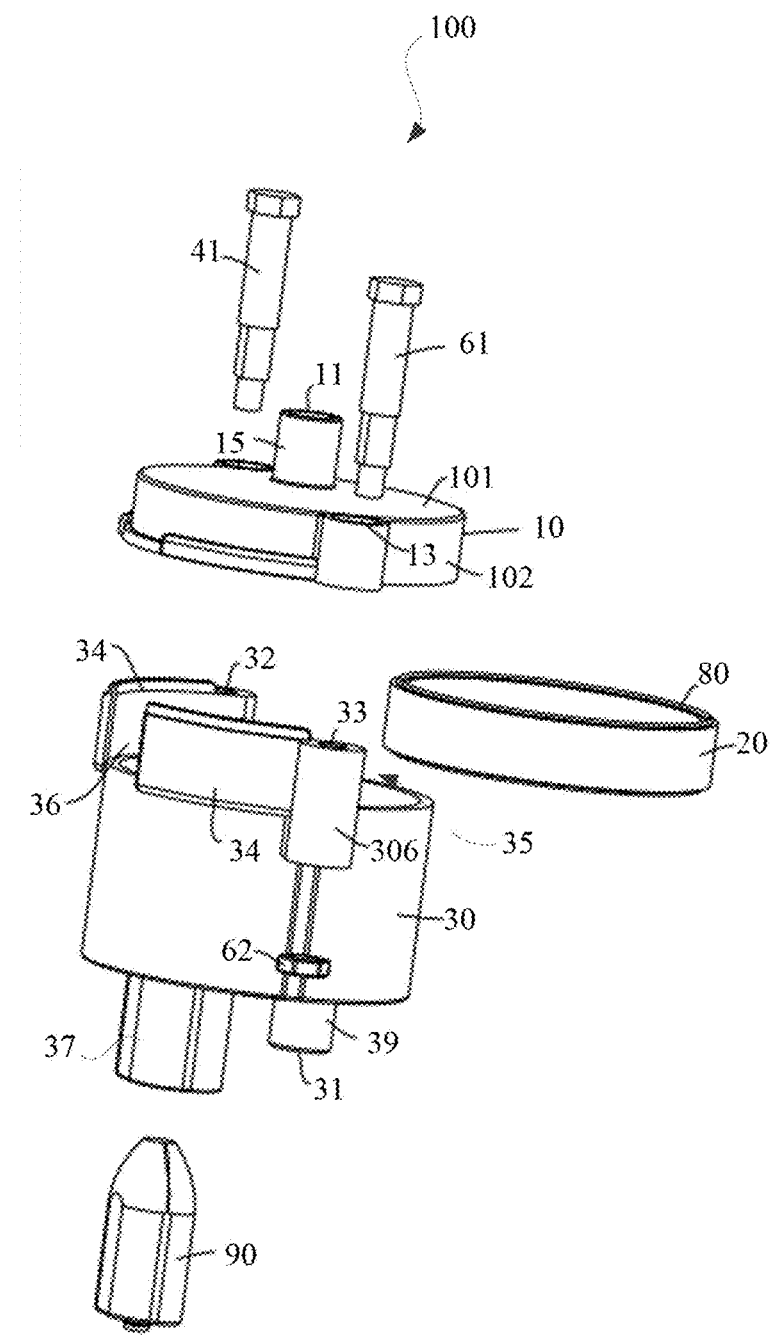
FIG. 14 is a schematic structural diagram of the another sample collecting device provided in embodiment 2 of the present application from a fourth perspective.
Figure 15:
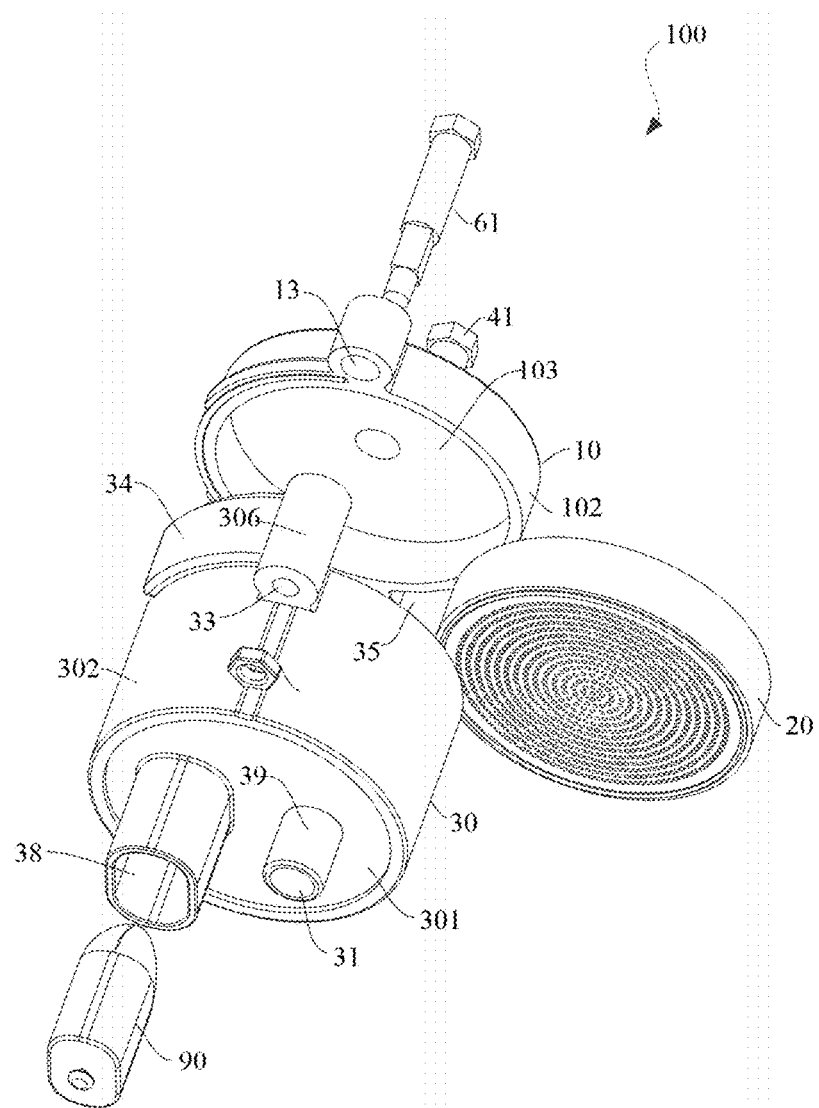
FIG. 15 is a schematic structural diagram of the another sample collecting device provided in Embodiment 2 of the present application from a fifth perspective.

Referring to FIGS. 9 and 10, in this embodiment, the cover body 10 is provided with a first hole 12, the filtering unit 20 is provided with a second hole 21 and the housing 30 is provided with a third hole 32. The first fastener 40 includes a first bolt 41 and a first nut 42. The first bolt 41 is threaded to the first nut 42 after passing through the first hole 12, the second hole 21 and the third hole 32.

It should be understood that the cover body 10, the filtering unit 20, and the housing 30 are all detachably connected through the first fastener 40, and thus the overall structure of the sample collecting device 100 is relatively compact.

Exemplarily, the first hole 12, the second hole 21 and the third hole 32 may all be a smooth hole, or part of the first hole 12, the second hole 21 and the third hole 32 may also be a threaded hole.

In order to prevent the first bolt 41 from self-rotation under force, as shown in FIG. 10, the third hole 32 may be a square hole or other non-circular hole, and an end of the first bolt 41 has a square cross-section or a cross-section adapted to the non-circular hole. In this way, after the cover body 10 is connected to the housing 30 through the first fastener 40, the first bolt 41 will not be self-rotated under force when the filtering unit 20 rotates relative to the cover body 10 or the housing 30.

In order to improve the sampling efficiency, as shown in FIG. 6 to FIG. 10, the sample collecting device 100 includes at least two filtering units 20, which are all connected to the first fastener 40 through a connecting part 22. Where, the second hole 21 is disposed on the connecting part 22 so that the first bolt 41 passes through the connecting part 22 and is threaded to the first nut 42.

Filtering units 20 are symmetrically arranged with respect to the first fastener 40 or the connecting part 22. In this way, a filtering unit 20 located in the cavity can be rotated to the outside of the housing assembly by rotating a fixed angle, and at the same time, a filtering unit 20 adjacent to this filtering unit 20 can be rotated in the cavity so as to participate in the extraction of the sample 300. This is convenient to control the rotation angle of the filtering units 20.

Exemplarily, referring to FIG. 6 to FIG. 10, the number of the filtering units 20 is two, and the two filtering units 20 are distributed symmetrically at an angle of 180 degrees. Alternatively, the number of the filtering units 20 in sample collecting device 100 can also be three, four, five, six or more. When the number of the filtering units 20 in the sample collecting device 100 is three, the three filtering units 20 are symmetrically distributed at an angle of 120 degrees with respect to the housing. When the number of the filtering units 20 in the sample collecting device 100 is four, the four filtering units 20 are distributed symmetrically at an angle of 90 degrees with respect to the housing assembly.

Figure 6:
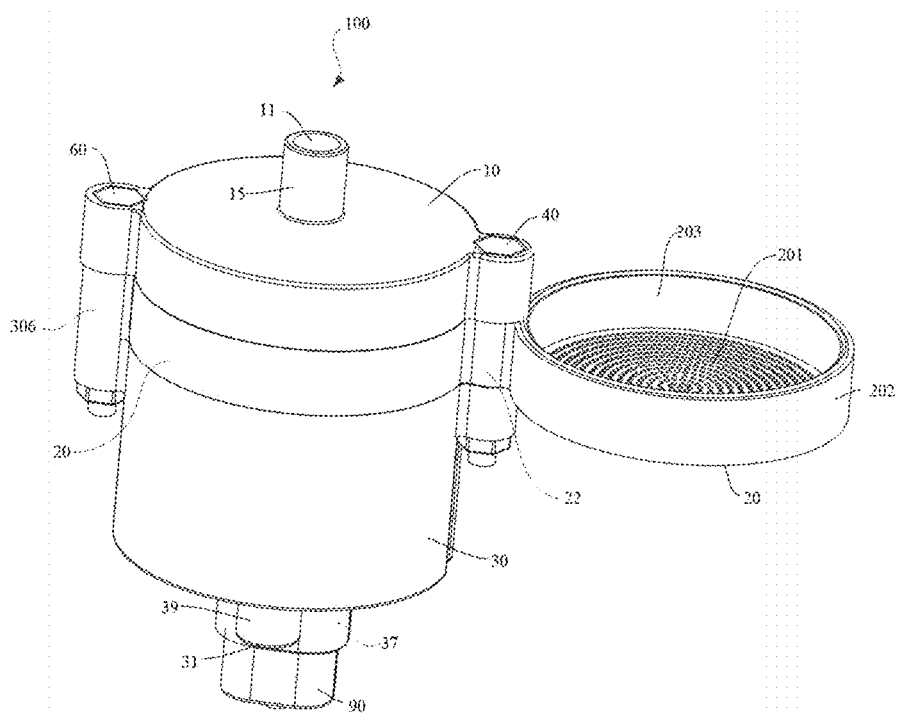
FIG. 6 is a schematic structural diagram of a sample collecting device provided in Embodiment 2 of the present application from a first perspective.
Figure 7:
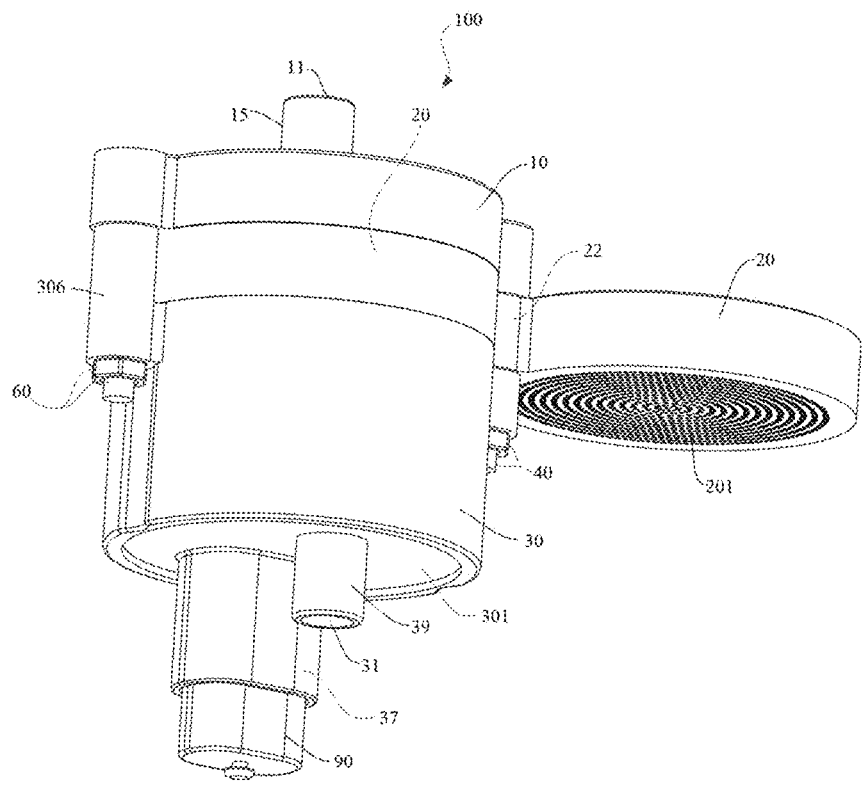
FIG. 7 is a schematic structural diagram of the sample collecting device provided in Embodiment 2 of the present application from a second perspective.
Figure 8:
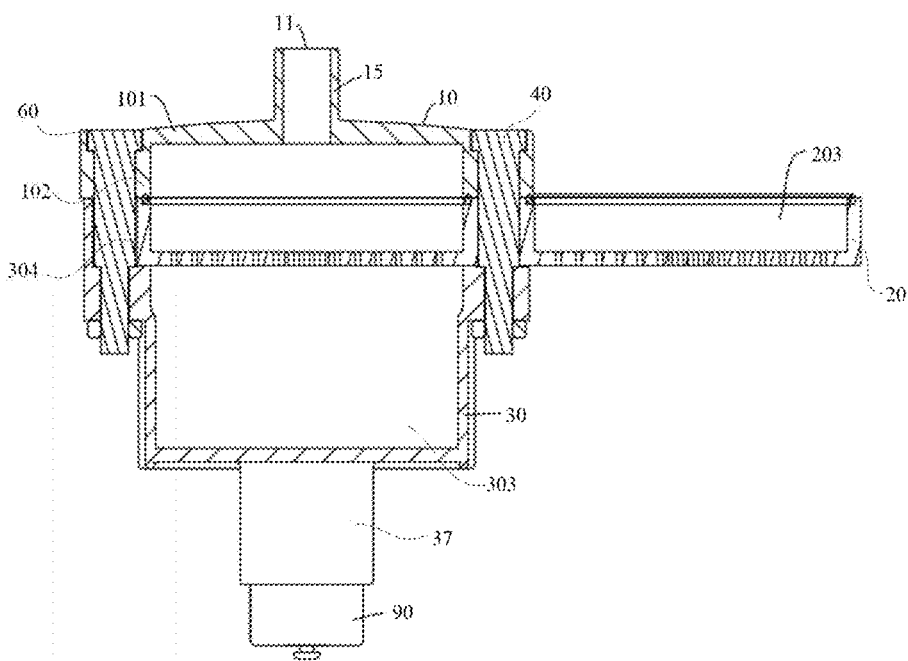
FIG. 8 is a schematic structural diagram of the sample collecting device provided in Embodiment 2 of the present application from a third perspective.

Taking the relative position in FIG. 6 for explanation, the filtering unit 20 on the left is located between the cover body 10 and the housing 30 and can collect the sample 300. The filtering unit 20 on the right is located outside the housing assembly. After the sample 300 is collected by the filtering unit 20 on the left and needs to be taken out, and the two filtering units 20 are rotated to interchange their positions. In this manner, the filtering unit 20 bearing no sample 300 rotates into the cavity and is located between the cover body 10 and the housing 30, and the filtering unit 20 bearing the sample 300 is completely located outside the housing assembly. At this time, the sample 300 may be taken away with tweezers or other tool.

Referring to 9 and 10, the cover body 10 is further provided with a fourth hole 13, and the housing 30 is further provided with a fifth hole 33. The sample collecting device 100 further includes a second fastener 60, the second fastener 60 includes a second bolt 61 and a second nut 62. The second bolt 61 is threaded to the second nut 62 after passing through the fourth hole 13 and the fifth hole 33. In this manner, through setting the second fastener 60, the cover body 10 and the housing 30 can be firmly connected to avoid a relative displacement between the cover body 10 and the housing 30 in use, affecting the air tightness of the sample collecting device 100.

It should be noted that, both the fourth hole 13 and the fifth hole 33 may be a smooth hole, or at least one of the fourth hole 13 and the fifth hole 33 may be a threaded hole.

The housing 30 is provided with a supporting member 306. Specifically, referring to FIGS. 6 to 16, the supporting member 306 is provided on the first side wall 302 of the housing 30 and extends toward one side of the cover body 10 and abuts against the cover body 10. In this way, the supporting member 306 can maintain a fixed distance between the housing 30 and the cover body 10 to avoid displacement between the cover body 10 and the housing 30.

On this basis, an installation process for the sample collecting device 100 is provided in this embodiment:

First, the cover body 10, the filtering unit 20, and the housing 30 are placed in sequence so that the first hole 12, the second hole 21 and the third hole 32 are aligned. Next, the first bolt 41 is connected and screwed to the first nut 42 after sequentially passing through the first hole 12, the second hole 21 and the third hole 32. At the same time, the second bolt 61 is connected and screwed to the second nut 62 after sequentially passing through the fourth hole 13 and the fifth hole 33.

It should be noted that the cooperation among the cover body 10, the filtering unit 20 and the housing 30 has certain requirements of air tightness. For example, when the suction reaches a negative pressure of 20 Kpa, the filtering unit 20 can still rotate relative to the cover body 10 or the housing 30.

When the sample 300 is taken out, the suction device is turned off at first, and then the filtering unit 20 is rotated to take out the sample 300 contained in the filtering unit 20. At the same time, the other filtering unit 20 bearing no sample 300 is moved into the cavity and placed between the cover body 30 and the housing 30 to participate in extracting the sample 300 and thus to collect continually other sample 300.

Further, referring to FIG. 6 to FIG. 16, the top of the housing assembly has a convex lens portion made of a transparent material. In other words, the cover body 10 has a convex lens portion made of a transparent material. In this way, the setting of the convex lens portion can enable the cover body 10 to have a magnifying function, which can facilitate the medical workers to observe tiny part of the sample 300 on the filtering unit 20.

Specifically, referring to FIGS. 6 to 16, the cover body 10 includes a top wall 101 and a second side wall 102 connected to the top wall 101. The second side wall 102 and the top wall 101 form a collecting tank 103 with an opening on one side. Where, the collecting hole 11 may be located at the center or eccentric position of the top wall 101 and communicated with the collecting tank 103. The top wall 101 is a convex lens portion. When the top wall 101 is a convex lens portion, the middle position of the top wall 101 is thicker and the edge position thereof is thinner. Therefore, the top wall may be regarded as a magnifying lens, which can realize the magnification function. Where, the eccentric position may be understood as a position offset from the center of the top wall 101, that is to say, the collecting hole is not located in the center position of the top wall.

The top wall 101 or the second side wall 102 of the cover body 10 is provided with a collecting hole 11, and the bottom wall 301 or the first side wall 302 of the housing 30 is provided with a suction hole 31. In this embodiment, the collecting hole 11 is provided on the top wall 101 of the cover body 10 and the suction hole 31 is provided on the bottom wall 301 of the housing 30. In this way, the above fluid can be quickly suctioned onto the filtering unit 20 through the collecting hole 11.

On the basis of the above embodiments, referring to FIGS. 11 to 16, a further sample collecting device 100 is provided in this embodiment, and the difference from the above sample collecting devices 100 is that the housing assembly further includes an enclosing member 34. The enclosing member 34 is located between the housing 30 and the cover body 10 and forms a cavity along with the housing 30 and the cover body 10. A gateway 304 is provided on the enclosing member 34. The filtering unit 20 is arranged in the cavity and is slidable relative to the gateway 304. In this way, the filtering unit 20 can be moved to the outside of the housing assembly through the gateway 304 in a sliding manner, and separated from the housing assembly. The filtering unit 20 may be directly disposed in the collecting bottle 200 to realize the collection of the sample 300 on the filtering unit 20 therein, without need to open the housing assembly and transfer the sample 300 in the filter unit 20 prior to collect the sample 300 into the collection bottle 200, which greatly improves the collection efficiency of the sample 300.

At the same time, through setting the enclosing member 34, on the one hand, it can facilitate the engagement and positioning of the filtering unit 20, so that the filtering unit 20 is located just between the cover body 10 and the housing 30, and on the other hand, it can ensure that the sample collecting device 100 has a certain degree of air tightness. Optionally, the number of the enclosing member may be two.

Further, referring to FIG. 11 to FIG. 16, the enclosing member 34 has a first gap 35 adapted to the filtering unit 20, and the first gap 35 forms the gateway 304. The filtering unit 20 is configured to slide to the outside of the housing assembly through the first gap 35. In this way, the filtering unit 20 can be moved to the outside of the housing assembly through the first gap 35 in a sliding manner, and is separated from the housing assembly, so that the filtering unit 20 may be directly disposed in the collecting bottle 200 for collecting the sample 300.

The first gap 35 forming the gateway 304 may be understood as the first gap 35, the enclosing member 34 and the housing assembly jointly defining the gateway 304.

It should be noted that when the sample 300 needs to be collected, the filtering unit 20 is stuck between the cover body 10 and the housing 30 in a sliding manner, and the cover body 10, the filtering unit 20 and the housing 30 are relatively fixed, so that normal collection of sample 300 may be realized. After the collection is completed, the filtering unit 20 may be separated from the housing assembly by sliding the filtering unit 20. At this time, the filtering unit 20 may be directly disposed in the collecting bottle 200, or the sample 300 on the filtering unit 20 may be removed with tweezers or other tool.

In order to facilitate the separation of the filtering unit 20 from the housing assembly, as shown in FIGS. 11 to 16, the enclosing member 34 further has a second gap 36, which is arranged opposite to the first gap 35. In this way, the medical workers can apply a force to the filtering unit 20 at the second gap 36 to facilitate the separation of the filtering unit 20 from the housing assembly.

In order to limit the position of the filtering unit 20 on the housing assembly, the opening of the second gap 36 is smaller than the opening of the first gap 35. In this way, when the filtering unit 20 is stuck between the cover body 10 and the housing 30 by sliding from the gateway 304, the position of the filtering unit 20 may be restricted through the second gap 36 to prevent the filtering unit 20 from continuing to slide.

It should be noted that the filtering unit 20 is stuck through the second gap 36 and is positioned under the action of the enclosing member 34. The operator can extend his/her hand into the first gap 35 to push the filter unit 20, which can make the filter unit 20 slide relative to the housing assembly, so that the filtering unit 20 is pushed out through the first gap 35.

The first gap 35 and the second gap 36 can be understood as openings on the enclosing member 34. Alternatively, two enclosing members 34 may be disposed in the sample collecting device 100 in this embodiment, and the first gap 35 and the second gap 36 may be formed between the two enclosing members 34. The filtering unit 20 may be separated from the cover body 10 through the first gap 35 and/or the second gap 36. In this embodiment, the formation modes of the first gap 35 and the second gap 36 are not further limited.

Optionally, the enclosing member 34 abuts against the cover body 10 so as to maintain a constant distance between the cover body 10 and the housing 30. The enclosing member 34 can maintain a stable connection between the cover body 10 and the housing 30 to a certain extent, so that the cover body 10 and the housing 30 are not easy to displace.

In order to ensure air tightness, a protrusion may be provided at the end of the enclosing member 34. A groove 307 is provided on ends of the cover body 10 and the housing 30 facing the enclosing member 34, and a sealing strip is provided in the groove 307. The enclosing member 34 is stuck into the groove 307 through the protrusion. In this way, the air tightness of the sample collecting device 100 is enhanced, and meanwhile the stability of the structure of the sample collecting device 100 is further increased.

On this basis, an installation process of the sample collecting device 100 is provided in this embodiment:

The filtering unit 20 is clamped into the enclosing member 34 and is located between the cover body 10 and the housing 30, so that the first hole 12 and the third hole 32 are aligned, and the fourth hole 13 and the fifth hole 33 are aligned. The first bolt 41 is connected and screwed to the first nut 42 after sequentially passing through the first hole 12 and the third hole 32; and the second bolt 61 is connected and screwed to the second nut 62 after sequentially passing through the fourth hole 13 and the fifth hole 33. Then the installation of the sample collecting device 100 is completed.

It should be noted that when the sample 300 needs to be taken out, the suction device may be closed first, the filtering unit 20 may be pushed out and inverted into the collecting bottle 200 to realize the separation of the sample 300. Then, the filtering unit 20 bearing no sample 300 is clamped into the enclosing member 34 through the second gap 36 and is located between the cover body 10 and the housing 30 so as to participate in the next extraction of sample 300.

Figure 16:
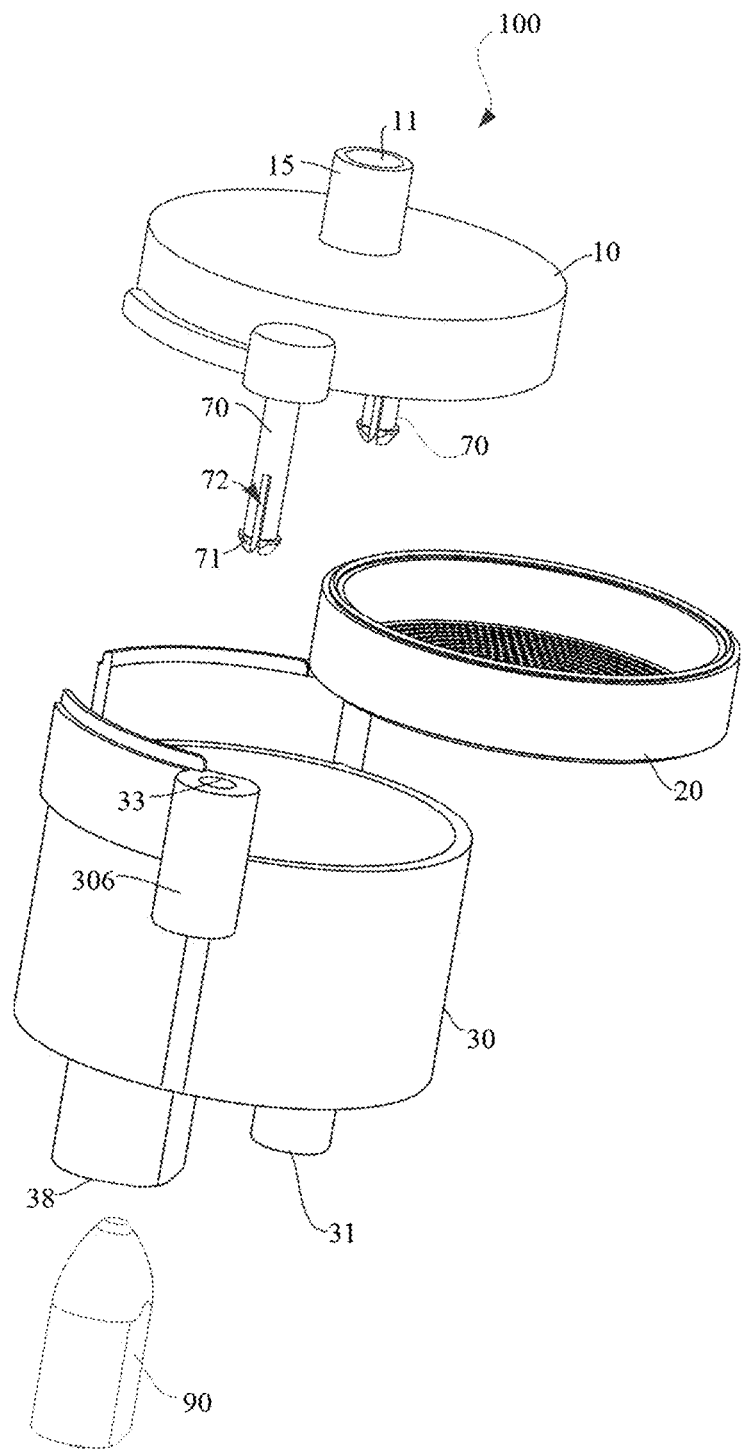
FIG. 16 is a schematic structural diagram of further another sample collecting device provided in Embodiment 2 of the present application from a first perspective.

As another possible embodiment, as shown in FIG. 16, the cover body 10 and the housing 30 may be detachably connected through a third fastener 70. For example, the number of the third fastener may be two, and the cover body 10 and the housing 30 may realize a stable connection by the two third fasteners 70. The difference of the third fastener 70 from the first fastener 40 and the second fastener 60 in this embodiment is that the third fastener 70 is provided with a chuck 71 at one end, and a notch 72 in the axial direction. In this way, the third fastener 70 has certain elasticity at one end having the chuck 71, so that the cover body 10 can be firmly connected to the housing 30 through the third fastener 70.

Specifically, when the chuck 71 is located in the fifth hole 33 or the third hole 32, the spacing of the third fastener 70 at the notch 72 is reduced, and the size of the chuck 71 is shrunk. When the chuck 71 extends out of the fifth hole 33 or the third hole 32, the size of the chuck 71 is restored, to clamp the housing 30, so that the cover body 10 and the housing 30 can realize a tight connection after the third fastener 70 passes through the fifth hole 33 or the third hole 32 via the chuck 71.

The other end of the third fastener 70 may be fixedly or detachably connected to the cover body 10. In this embodiment, the manner of connection between the third fastener 70 and the cover body 10 is not further limited.

It should be understood that the cover body 10 may also be connected to the housing 30 by clamping, welding, gluing or other fastener. Exemplarily, other fastener includes but is not limited to bolts, screws or pins. Theoretically, any method for fixing both the cover body 10 and the housing 30 may be selected in the prior art.

In order to further enhance the air tightness of the sample collecting device 100, as shown in FIG. 6 to FIG. 17, the filtering unit 20 is connected to at least one of the housing 30 and the cover body 10 through a sealing member 80. The sealing member 80 is arranged on a side of the filtering unit 20 close to the cover body 10, and/or arranged on a side of the filter uniting 20 close to the housing 30. In this way, through the setting of the sealing member 80, the air tightness of coordination among the cover body 10, the filtering unit 20 and the housing 30 can be further improved, which is conducive to the extraction of the sample 300 in the sample collecting device 100.

Specifically, the sealing member 80 may be located above the filtering unit 20 to seal the space between the cover body 10 and the filtering unit 20. The sealing member 80 may also be located below the filtering unit 20 to seal the space between the filtering unit 20 and the housing 30.

Exemplarily, the sealing member 80 includes but is not limited to a seal ring or a seal strip.

The sample collecting device provided in this embodiment can greatly simplify the collection of samples, and realize rapid collection of samples, and the recovery process is more convenient. This greatly improves the collection efficiency and at the same time, can realize continuous sample collection, and has the advantages of multi-function, economy, safety and convenience, etc.

Embodiment 3

Figure 17:
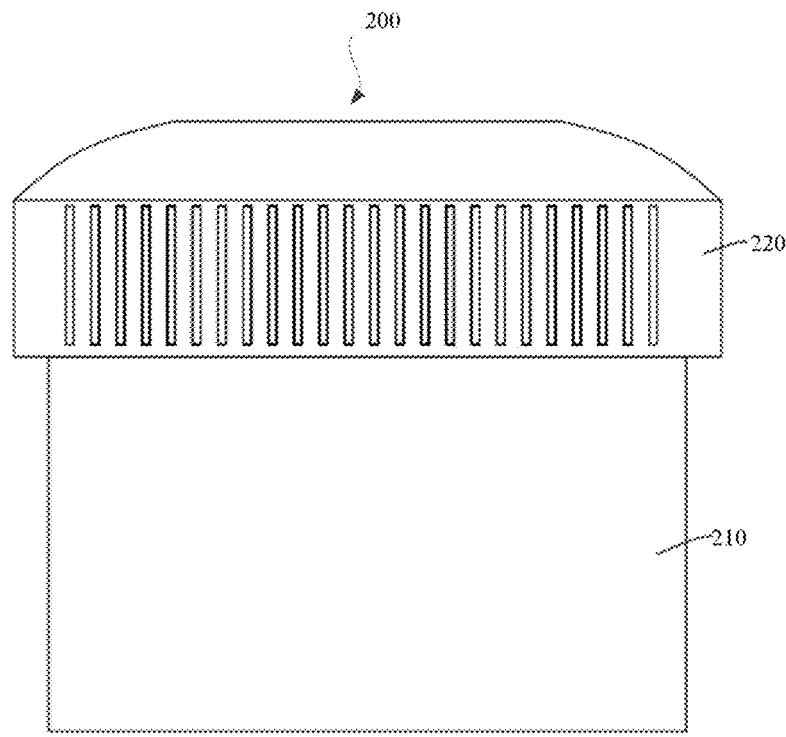
FIG. 17 is a schematic structural diagram of a collecting bottle provided in Embodiment 3 of the present application.
Figure 18:
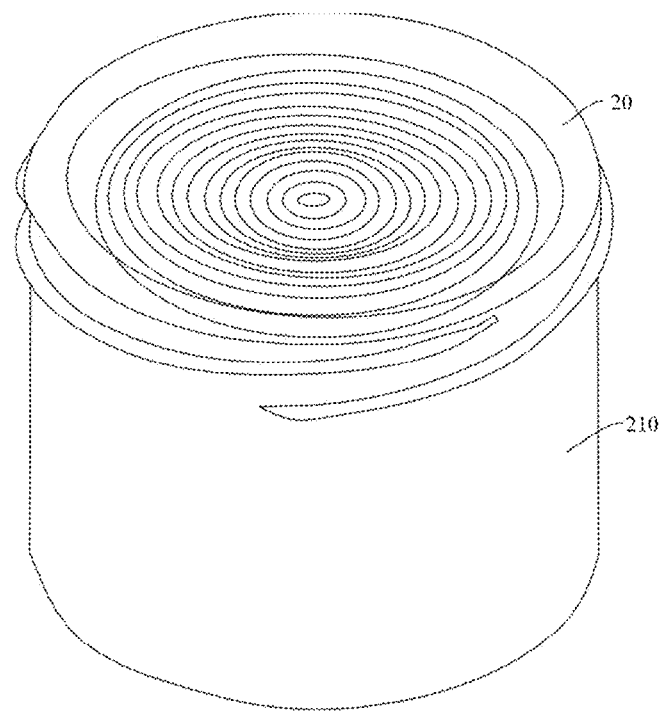
FIG. 18 is a schematic structural diagram of a bottle body of the collecting bottle shown in FIG. 17 from a first perspective.
Figure 19:
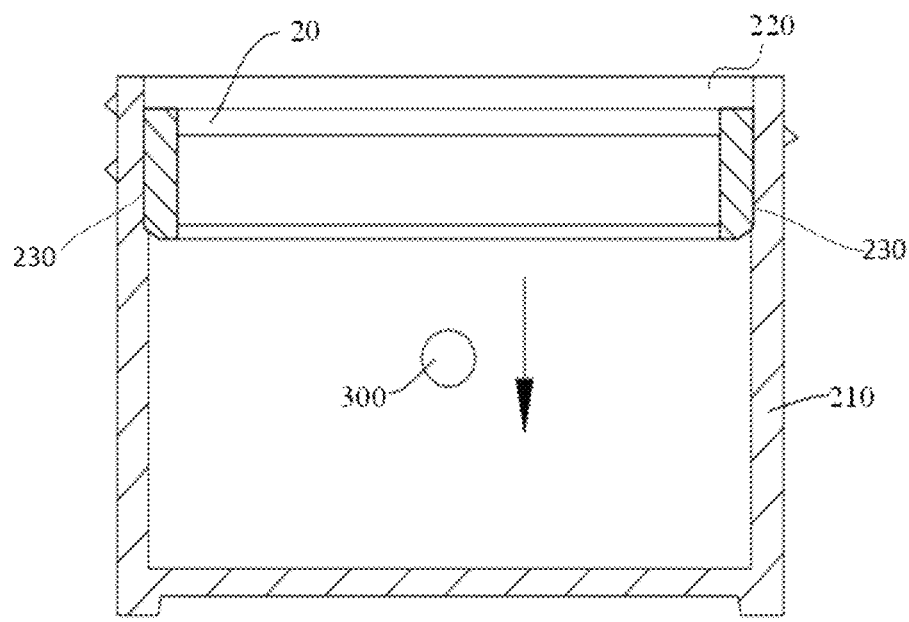
FIG. 19 is a schematic structural diagram of the bottle body of the collecting bottle shown in FIG. 17 from a second perspective.

FIG. 17 is a schematic structural diagram of a collecting bottle provided in Embodiment 3 of the present application, FIG. 18 is a schematic structural diagram of a bottle body of the collecting bottle shown in FIG. 17 from a first perspective, and FIG. 19 is a schematic structural diagram of the bottle body of the collecting bottle shown in FIG. 17 from a second perspective.

On the basis of the foregoing Embodiment 1 and Embodiment 2, referring to FIG. 17 to FIG. 19, a sample collecting apparatus is provided in this embodiment of the present application. The sample collecting apparatus includes a collecting bottle 200 and any one of the foregoing sample collecting devices 100. The collecting bottle 200 has an assembly port that is adapted to the filtering unit 20 of the sample collecting devices 100. In this way, the filtering unit 20 can be directly disposed in the collecting bottle 200, so as to complete the collection of the sample 300 in the collecting bottle 200.

It should be noted that the sample collecting device 100 in this embodiment may refer to the related descriptions of the sample collecting devices 100 in the above Embodiments 1 and 2. The sample collecting device 100 in this embodiment includes all the functions of the sample collecting devices 100 in the above embodiments. The structure of the sample collecting device 100 will not be further described in this embodiment.

Further, referring to FIG. 17 to FIG. 19, the collecting bottle 200 further includes a bottle lid 220 that is hermetically connected to the bottle body 210 of the collecting bottle 200. The bottle body 210 has an assembly port that is adapted to the filtering unit 20, and the assembly port of the bottle body 210 is provided with a step portion. In this manner, the filtering unit 20 is just relatively fixed with the bottle body 210 after being inverted, and cannot continue to move into the bottle body 210, which is also convenient to take out the filtering unit 20.

As shown in FIG. 19, after the filtering unit 20 bearing the sample 300 is inverted into the bottle body 210, the opening of the bottle body 210 is closed by the bottle lid 220, and the collecting bottle 200 is turned upside down, and formalin flowing in the bottle flushes down the sample 300 on the filtering unit 20 to complete the collection of the sample 300.

Specifically, the sample collecting apparatus further includes a suction device, a pipe connected with the suction device, an endoscopic forceps, and a pipe connected with the endoscopic forceps, and so on.

This application provides a sample collecting device and a sample collecting apparatus. At least part of the filtering unit can be moved to the outside of the housing assembly relative to the housing assembly. This simplifies the sample collection process and helps to quickly take out the sample on the filtering unit and transfer it to the collecting bottle of the sample collecting apparatus, thus improving the efficiency of sample collection and thereby effectively saving the time of sample separation and collection.

In the description of the present application, it should be understood that orientations or positional relationships indicated by terms such as "center", "length", "width", "thickness", "above", "below", "front", "rear", "left", "right", "vertical", "horizontal", "top", "bottom", "inner", and "outer" is based on the orientations or positional relationships shown in the accompanying drawings, and is only for the convenience of describing the present application and simplifying the description, rather than indicating or implying that the device or element indicated must have a specific orientation or be constructed and operated in a specific orientation, so they cannot be understood as a limitation to the present application.

In the description of this application, it should be understood that the terms "including", "comprising" and "having" and any variations thereof used herein are intended to cover non-exclusive inclusions. For example, a process, method, system, product or apparatus including a series of steps or units needs not be limited to those clearly listed, but may include other step or unit not clearly listed or inherent to such process, method, product or apparatus.

Unless otherwise clearly specified and defined, the terms "installation", "connecting", "connected", "fixing", etc. should be understood in a broader sense. For example, it may be a fixed connection, a detachable connection, or integrated as a whole; it may be direct connection, or indirect connection through an intermediate medium; or it may be the internal communication between two elements or the interaction between the two elements. For those of ordinary skill in the art, the specific meanings of the above terms in the present application may be understood according to specific circumstances. In addition, the terms "first", "second", etc. are only intended for descriptive purposes, and cannot be understood as indicating or implying relative importance or implicitly indicating the number of indicated technical features.

Finally, it should be noted that the foregoing embodiments are merely intended for describing the technical solutions of the present application other than limiting the present application. Although the present application is described in detail with reference to the foregoing embodiments, persons of ordinary skill in the art should understand that they may still make modifications to the technical solutions described in the foregoing embodiments or make equivalent substitutions to some or all technical features therein, and these modifications and substitutions will not make the essence of corresponding technical solutions depart from the range of the technical solutions of various embodiments of the present application.

What is claimed is:

1. A sample collecting device, comprising a housing assembly and a filtering unit, wherein the housing assembly has a cavity and is provided with a collecting hole and a suction hole, both the collecting hole and the suction hole are communicated with the cavity, the filtering unit is provided in the cavity, the suction hole is communicated with the collecting hole through the filtering unit, the housing assembly is provided with a gateway on its side wall; and at least part of the filtering unit is configured to be moved to an outside of the housing assembly through the gateway, so that a sample in the filtering unit is taken out.

2. The sample collecting device according to claim 1, wherein in a horizontal direction of the housing assembly, the filtering unit is movably arranged relative to the housing assembly.

3. The sample collecting device according to claim 1, wherein the housing assembly comprises a housing and a cover body, the cover body is arranged and covered on an open end of the housing, at least part of the filtering unit is located in the housing or the filtering unit is located between the housing and the cover body.

4. The sample collecting device according to claim 3, wherein the collecting hole is provided on a top wall or a side wall of the cover body and the suction hole is provided on a bottom wall or a side wall of the housing.

5. The sample collecting device according to claim 3, wherein the housing has the cavity, the side wall of the housing is provided with the gateway, the gateway is adapted to the filtering unit and communicated with the cavity each other, and the filtering unit is configured to be moved to the gateway relative to the housing assembly.

6. The sample collecting device according to claim 5, wherein the filtering unit is rotatably disposed relative to the housing, or the filtering unit is slidably disposed relative to the housing.

7. The sample collecting device according to claim 6, wherein when the filtering unit is rotatably disposed relative to the housing, the sample collecting device comprises at least two filtering units, at least one rotation assembly is provided in the housing, the rotation assembly is rotatably disposed in the cavity relative to the housing and has two oppositely arranged support portions, and the filtering units are arranged on the support portions and detachably connected to the rotation assembly.

8. The sample collecting device according to claim 7, wherein the rotation assembly comprises a rotation member and the support portions; the support portions are provided on two opposite sides of the rotation member, the rotation member is rotatably disposed relative to the housing, the rotation member, the housing and the cover body form a suction cavity communicated with the collecting hole, the gateway is located outside the suction cavity and one of the support portions of the rotation assembly is located in the suction cavity.

9. The sample collecting device according to claim 8, wherein the rotation member comprises a rotating portion rotatably connected to a middle of a bottom wall of the housing, and the rotation member is rotatably arranged around the rotating portion relative to the housing; or
wherein the rotation member has a driving portion which protrudes from the cover body, and/or a peripheral edge of the rotation member is hermetically connected with an inner side wall of the housing assembly.

10. The sample collecting device according to claim 7, wherein a through hole is provided at bottoms of the support portions, and the suction hole is communicated with the collecting hole through the support portions and the filtering unit.

11. The sample collecting device according to claim 6, wherein when the filtering unit is slidably disposed relative to the housing, a bearing part is provided in the housing, part of the filtering unit is supported in the cavity by the bearing part, and the filtering unit is slidably arranged relative to the gateway.

12. The sample collecting device according to claim 11, wherein a chute adapted to the side wall of the filtering unit is provided on an inner side wall of the housing.

13. The sample collecting device according to claim 12, wherein a height of the side wall of the filtering unit is gradually decreased in a direction toward the bearing part.

14. The sample collecting device according to claim 11, wherein the bearing part is a step structure on an inner side wall of the housing, and an edge of the filtering unit is supported on the step structure.

15. The sample collecting device according to claim 6, wherein when the filtering unit is slidably disposed relative to the housing, the filtering unit comprises a sealing end, and the filtering unit is hermetically connected with the housing at the gateway by the sealing end.

16. The sample collecting device according to claim 3, wherein the cover body is connected to the housing, the cover body and the housing form the cavity, the gateway is formed between the housing and the cover body, and the filtering unit is located in and blocks the gateway.

17. The sample collecting device according to claim 16, wherein a gap is provided between the cover body and the housing, the gap forms the gateway, and the filtering unit is disposed in the gateway and abuts against the cover body and the housing.

18. The sample collecting device according to claim 16, wherein the filtering unit is rotatably or slidably disposed relative to the housing assembly.

19. The sample collecting device according to claim 18, wherein the cover body is detachably connected to the housing through a first fastener, and the filtering unit is connected to the first fastener and is rotatable around the first fastener relative to the housing assembly.

20. The sample collecting device according to claim 19, wherein the sample collecting device comprises at least two filtering units, the at least two filtering units are connected to the first fastener by a connecting part, and/or, the at least two filtering units are symmetrically arranged with respect to the first fastener.

21. The sample collecting device according to claim 18, wherein the housing assembly further comprises an enclosing member, the enclosing member is located between the housing and the cover body, and the enclosing member forms the cavity along with the housing and the cover body, the enclosing member is provided with the gateway, and the filtering unit is arranged in the cavity and is slidably arranged relative to the gateway;

wherein the filtering unit is located inside the enclosing member, the enclosing member has a first gap adapted to the filtering unit, the first gap forms the gateway, and the filtering unit is configured to slide to the outside of the housing assembly through the first gap.

22. The sample collecting device according to claim 21, wherein the enclosing member further has a second gap, which is arranged opposite to the first gap.

23. The sample collecting device according to claim 22, wherein an opening of the second gap is smaller than an opening of the first gap.

24. The sample collecting device according to claim 16, wherein the filtering unit is hermetically connected to at least one of the housing and the cover body through a sealing member.

25. A sample collecting apparatus, comprising a collecting bottle and the sample collecting device according to claim 1, wherein the collecting bottle is provided with an assembly port adapted to the filtering unit of the sample collection device.

* * * * *